US008940883B2

(12) United States Patent
Gruber et al.

(10) Patent No.: US 8,940,883 B2
(45) Date of Patent: *Jan. 27, 2015

(54) ANTI-FXI ANTIBODIES AND METHODS OF USE

(71) Applicants: Oregon Health & Science University, Portland, OR (US); Vanderbilt University, Nashville, TN (US)

(72) Inventors: Andras Gruber, Portland, OR (US); Erik I. Tucker, Portland, OR (US); David Gailani, Franklin, TN (US)

(73) Assignees: Oregon Health & Science University, Portland, OR (US); Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/755,322

(22) Filed: Jan. 31, 2013

(65) Prior Publication Data

US 2013/0129745 A1 May 23, 2013

Related U.S. Application Data

(63) Continuation of application No. 13/140,115, filed as application No. PCT/US2009/068768 on Dec. 18, 2009, now Pat. No. 8,388,959.

(60) Provisional application No. 61/138,590, filed on Dec. 18, 2008.

(51) Int. Cl.
*C07H 21/04* (2006.01)
*C07K 16/36* (2006.01)
*A61K 39/00* (2006.01)

(52) U.S. Cl.
CPC ........... *C07K 16/36* (2013.01); *A61K 2039/505* (2013.01); *C07K 2316/96* (2013.01)
USPC .................. 536/23.53; 424/133.1; 424/141.1; 424/145.1; 530/387.3; 530/388.25; 435/328; 435/337

(58) Field of Classification Search
None
See application file for complete search history.

(56) References Cited

U.S. PATENT DOCUMENTS

2006/0057140 A1  3/2006  Feuerstein
2006/0073535 A1*  4/2006  Greenfield et al. .......... 435/7.92
2008/0138837 A1*  6/2008  Greenfield et al. .......... 435/7.21

FOREIGN PATENT DOCUMENTS

WO      WO 0007626 A1 *   2/2000
WO    WO 2009046274 A1 *  4/2009
WO    WO 2009/067660       5/2009

OTHER PUBLICATIONS

Baglia et al., "Functional domains in the heavy-chain region of factor XI: a high molecular weight kininogen-binding site and a substrate-binding site for factor IX," *Blood*, vol. 74(1):244-251, 1989.
Douglas et al., "Vitamin C for Preventing and Treating the Common Cold (Review)," *Cochrane Database Syst. Rev*6., Issue 4, Art. No. CD000980, 2004.
Gruber et al., "Factor XI-Dependence of Surface-and Tissue Factor-Initiated Thrombus Propagation in Primates," *Blood*, vol. 102(3):953-955, 2003.
Kravtsov et al., "Factor XI Contributes to Thrombin Generation in the Absence of Factor XII," *Blood*, vol. 114(2):452-458, 2009.
Lisman, "Factor XI Binding to Platelets, Glycoprotein Ibα Has an Accomplice," *Arterioscler Thromb Vasc Biol*, vol. 29:1409-1410, 2009.
Meijers, "Feedback controversy stops here," *Blood*, vol. 114(2):235, 2009.
Nishikado et al., "Murine Monoclonal Antibodies to Human Factor XI," *Thromb. Res.*, vol. 42:225-234, 1986.
Sinha et al., "Functional Characterization of Human Blood Coagulation Factor Xia Using Hybridoma Antibodies," *J. Biol. Chem.*, vol. 260:10714-10719, 1985.
Sri et al., "Generalized Verrucosis: A Review of the Associated Diseases, Evaluation, and Treatments," *J. Am. Acad. Dermatol.*, vol. 66(2):292-311, 2012.
Tucker et al., "Survival Advantage of Coagulation Factor XI-Deficient Mice during Peritoneal Sepsis," *J Infect Dis*, vol. 198(2):271-274, 2008.
Tucker et al., "Prevention of Vascular Graft Occlusion and Thrombus-Associated Thrombin Generation by Inhibition of Factor XI," *Blood*, vol. 113(4):936-944, 2009.
White-Adams et al., "Identification of Coagulation Factor XI as a Ligand for Platelet Apolipoprotein E Receptor 2 (ApoER2)," *Arterioscler Thromb Vasc Biol*, vol. 29:1602-1607, 2009.
Baglia et al., "A Binding Site for Thrombin in the Apple 1 Domain of Factor XI," *J. Biol. Chem.*, vol. 271:3652-3658, 1996.
Yamashita et al., "Factor XI Contributes to Thrombus Propagation on Injured Neointima of the Rabbit Iliac Artery," *J. Thromb. Haemost.*, vol. 4:1496-1501, 2006.

* cited by examiner

*Primary Examiner* — Michael Szperka
(74) *Attorney, Agent, or Firm* — Klarquist Sparkman, LLP

(57) ABSTRACT

Disclosed herein are monoclonal antibodies specific for factor XI (fXI) that prevent activation of fXI by factor XIIa (fXIIa). The monoclonal antibodies are universal fXI antibodies, capable of binding all mammalian species tested. The anti-fXI monoclonal antibodies prolong clotting time in mammalian plasmas. Moreover, administration of the fXI monoclonal antibodies disclosed herein results in inhibition of thrombosis without altering hemostasis in animal models of thrombosis. Thus, provided herein are monoclonal antibodies specific for fXI that block activation of fXI by fXIIa, compositions and immunoconjugates comprising such antibodies and their methods of use.

12 Claims, 10 Drawing Sheets

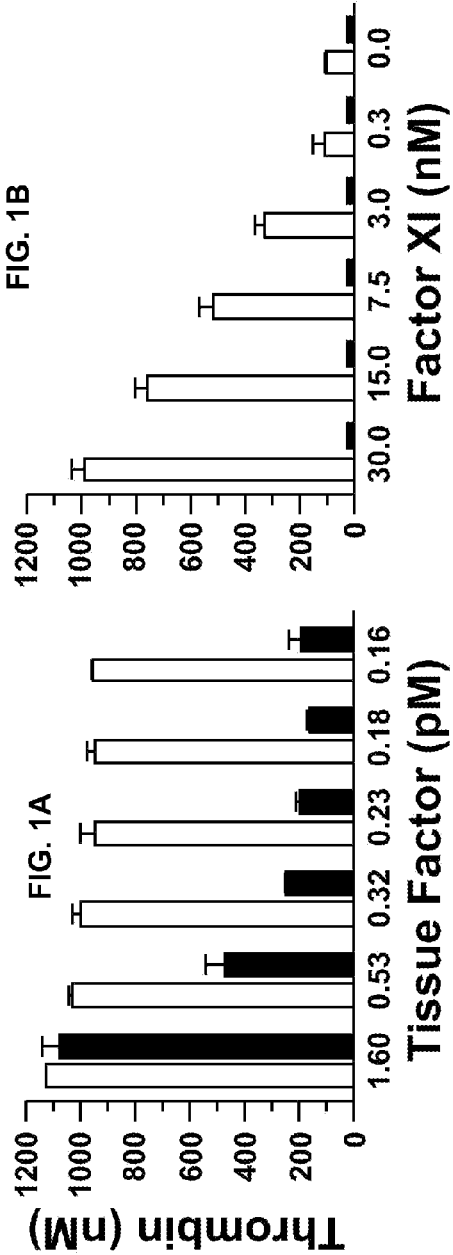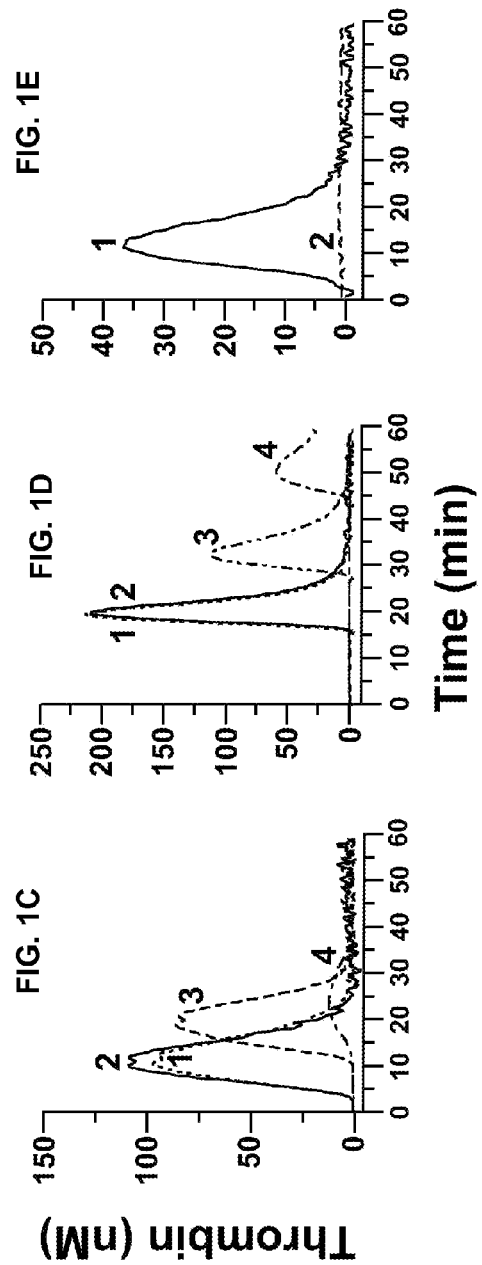

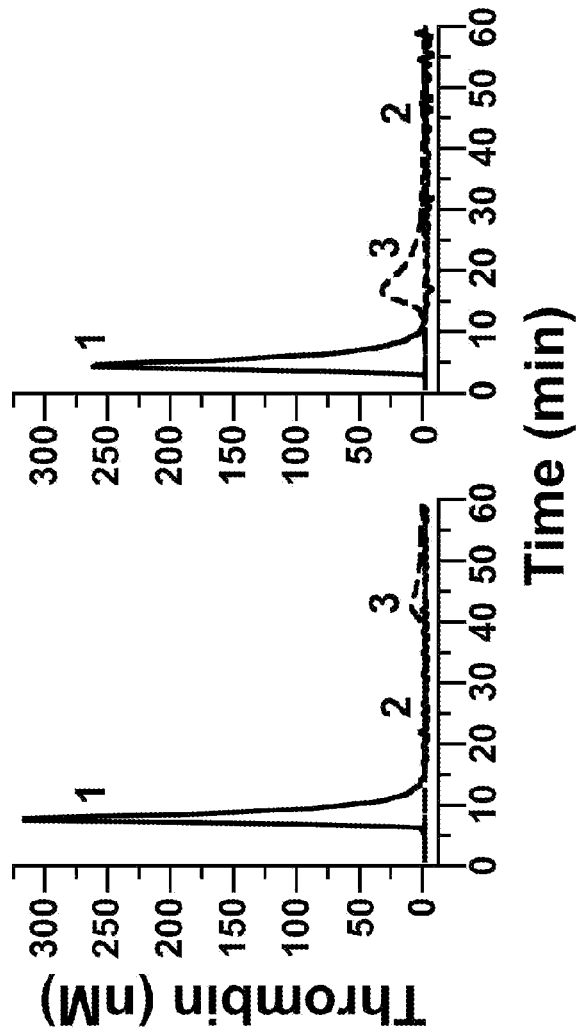
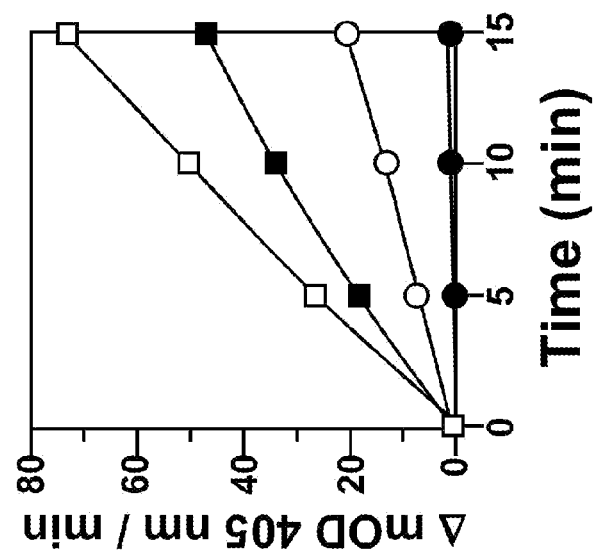
FIG. 3A
FIG. 3B
FIG. 3C

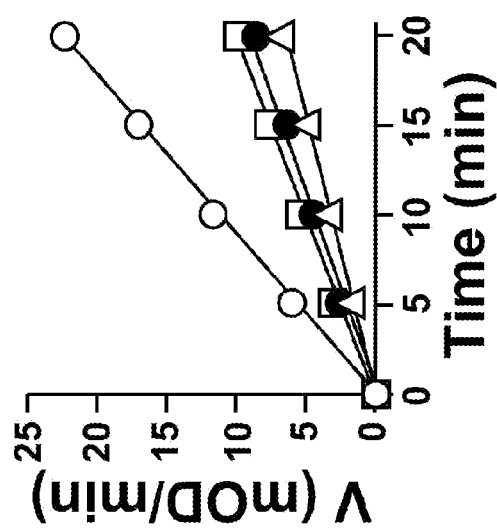
FIG. 5A
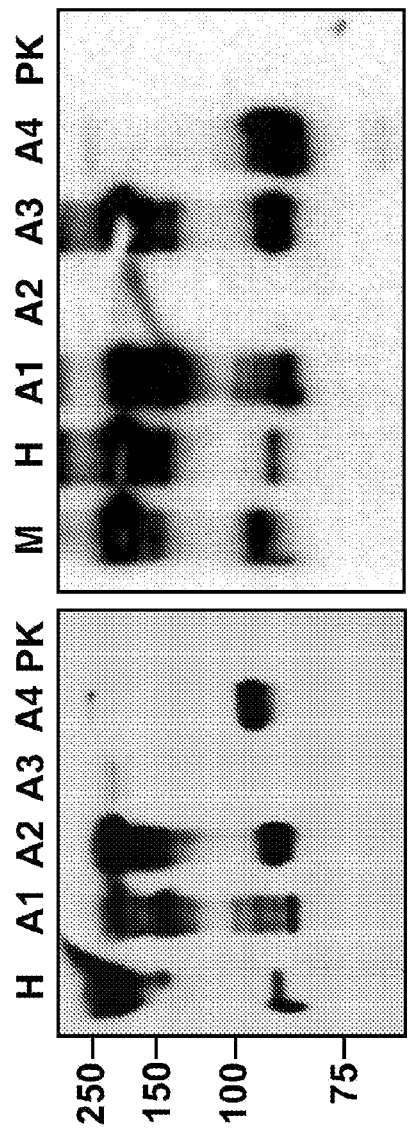
FIG. 5B
FIG. 5C

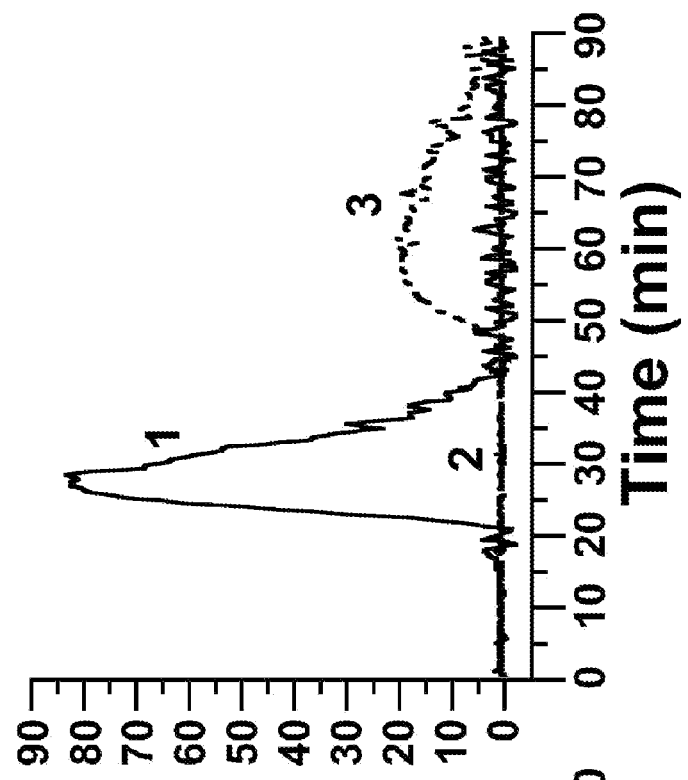
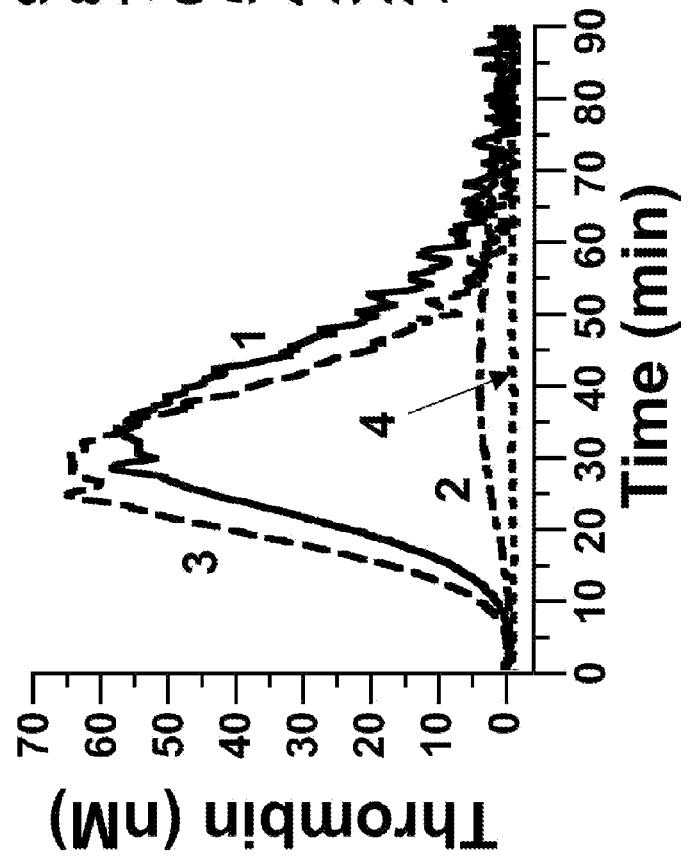
FIG. 7A
FIG. 7B

SEQUENCE LISTING

```
<160> NUMBER OF SEQ ID NOS: 4

<210> SEQ ID NO 1
<211> LENGTH: 108
<212> TYPE: PRT
<213> ORGANISM: Artificial Sequence
<220> FEATURE:
<223> OTHER INFORMATION: Immunoglobulin variable light chain
<220> FEATURE:
<221> NAME/KEY: MISC_FEATURE
<222> LOCATION: (24)..(34)
<223> OTHER INFORMATION: CDR1
<220> FEATURE:
<221> NAME/KEY: MISC_FEATURE
<222> LOCATION: (50)..(63)
<223> OTHER INFORMATION: CDR2
<220> FEATURE:
<221> NAME/KEY: MISC_FEATURE
<222> LOCATION: (91)..(98)
<223> OTHER INFORMATION: CDR3

<400> SEQUENCE: 1

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Leu Thr Ser Tyr Arg Asn Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80
```

Glu Asp Leu Ala Val Tyr Tyr Cys Gln Gln His Tyr Lys Thr Pro Tyr
                85                  90                  95

Ser Phe Gly Gly Gly Thr Lys Leu Glu Arg Leu Arg
            100                 105

<210> SEQ ID NO 2
<211> LENGTH: 324
<212> TYPE: DNA
<213> ORGANISM: Artificial Sequence
<220> FEATURE:
<223> OTHER INFORMATION: Immunoglobulin variable light chain

<400> SEQUENCE: 2
gacattgtga tgacccagtc tcacaaattc atgtccacat cagtaggaga cagggtcagc      60
atcacctgca aggccagtca ggatgtgagt actgctgttg cctggtatca acagaaacca     120
ggacaatctc ctaaactact gatttacttg acatcctacc ggaacactgg agtccctgat     180
cgcttcactg gcagtggatc tgggacggat ttcactttca ccatcagcag tgtgcaggct     240
gaagacctgg cagtttacta ctgtcagcaa cattataaaa ctccgtattc gttcggaggg     300
gggaccaagc tggaacggtt acgg                                            324

<210> SEQ ID NO 3
<211> LENGTH: 116
<212> TYPE: PRT
<213> ORGANISM: Artificial Sequence
<220> FEATURE:
<223> OTHER INFORMATION: Immunoglobulin variable heavy chain
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(68)
<223> OTHER INFORMATION: CDR2
<220> FEATURE:
<221> NAME/KEY: MISC_FEATURE
<222> LOCATION: (98)..(105)
<223> OTHER INFORMATION: CDR3

<400> SEQUENCE: 3

Gln Val Gln Leu Glu Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Ile Tyr Trp Val Arg Gln Pro Pro Gly Lys Gly Leu Glu Trp Leu
        35                  40                  45

Gly Met Ile Trp Gly Asp Gly Arg Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Tyr Tyr Gly Ser Lys Asp Tyr Trp Gly Gln Gly Thr Thr Leu
            100                 105                 110

Thr Val Ser Ser
        115

<210> SEQ ID NO 4
<211> LENGTH: 348
<212> TYPE: DNA

```
<213> ORGANISM: Artificial Sequence
<220> FEATURE:
<223> OTHER INFORMATION: Immunoglobulin variable heavy chain

<400> SEQUENCE: 4
caggtgcagc tggaggagtc aggacctggc ctggtggcgc cctcacagag cctgtccatc      60
acatgcaccg tctcagggtt ctcattaacc ggctatggta tatactgggt tcgccagcct     120
ccaggaaagg gtctggagtg gctgggaatg atatggggtg atggaagaac agactataat     180
tcagctctca aatccagact gagcatcagt aaggacaact ccaagagcca agttttctta     240
aaaatgaaca gtctgcaaac tgatgacaca gccaggtact actgtgccag agattactac     300
ggtagtaagg actactgggg ccaaggcacc actctcacag tctcctca                  348
```

ANTI-FXI ANTIBODIES AND METHODS OF USE

CROSS REFERENCE TO RELATED APPLICATIONS

This is a continuation of U.S. application Ser. No. 13/140,115, filed Jun. 16, 2011, issued as U.S. Pat. Ser. No. 8,388,959 on Mar. 5, 2013, which is the U.S. National Stage of International Application No. PCT/US2009/068768, filed Dec. 18, 2009, published in English under PCT Article 21(2), which claims the benefit of U.S. Provisional Application No. 61/138,590, filed on Dec. 18, 2008. The above-listed applications are incorporated herein by reference in their entirety.

ACKNOWLEDGMENT OF GOVERNMENT SUPPORT

This invention was made with government support under grant numbers HL58837 and HL81326 awarded by the National Heart, Lung and Blood Institute of the National Institutes of Health. The government has certain rights in the invention.

FIELD

This disclosure concerns monoclonal antibodies specific for coagulation factor XI (fXI) and their methods of use.

BACKGROUND

Thrombosis is a general term for diseases caused by the localized accumulation of circulating blood elements within the vasculature that result in vessel occlusion. Conventional antithrombotic drugs can inhibit thrombus growth by targeting coagulation pathways (for example, heparin and warfarin) or platelet-dependent mechanisms (such as aspirin or clopidogrel). Thrombolytic agents (e.g., streptokinase) are used to degrade thrombi in situ to restore blood flow. Despite advances in this field, the search for new strategies continues because existing treatments impair hemostasis, and must be administered at doses that do not achieve maximum efficacy (Gruber and Hanson, *Curr. Pharm. Des.* 9(28):2367-2374, 2003).

Hemostasis is a vital function that stops bleeding and protects the integrity of blood circulation on both molecular and macroscopic levels. Hemostasis includes a coagulation cascade of sequentially activatable enzymes that is traditionally divided into three parts: (1) an intrinsic pathway, which includes interactions of blood coagulation proteins that lead to the generation of coagulation factor IXa without involvement of coagulation factor VIIa; (2) an extrinsic pathway, which includes interactions of blood coagulation proteins that lead to the generation of coagulation factor Xa and/or IXa without involvement of factor XI; and (3) a common coagulation pathway, including interactions of blood coagulation proteins II, V, VIII, IX and X that lead to the generation of thrombin. Thrombin activates platelets and generates fibrin, both of which are essential building elements of the hemostatic plug that is responsible for sealing the vascular breach. Complete absence of thrombin or platelets causes paralysis of hemostasis and leads to lethal hemorrhage.

The plasmas of placental and marsupial mammals contain factor XI (fXI) (Ponczek et al., *J. Thromb. Haemost.* 6:1876-1883, 2008), the zymogen of a plasma protease (fXIa) that contributes to fibrin formation and stability through factor IX activation (Furie et al., *Hematology: Basic Principles and Practice*, 4th ed. New York: Churchill Livingstone 1931, 2005). fXI deficiency causes a variable trauma-induced hemorrhagic disorder in humans and other species (Seligsohn et al., *Thromb. Haemost.* 98:84-89, 2007; Knowler et al., *J. Am. Vet. Med. Assoc.* 205:1557-61, 1994; Ghanem et al., *J. Vet. Med. Sci.* 67:713-715, 2005; Troxel et al., *J. Am. Anim. Hosp. Assoc.* 38:549-553, 2002). The physiologic mechanism by which fXI is converted to fXIa has been a topic of debate (Pedicord et al., *Proc. Natl. Acad. Sci. U.S.A.* 104:12855-12860, 2007; Blat & Seiffert, *Thromb. Haemost.* 99:457-460, 2008). When blood is exposed to a charged surface, the process of contact activation converts factor XII (fXII) to the protease fXIIa, which then activates fXI (Gailani and Broze, *Metabolic and Molecular Basis of Inherited Disease*, Scriver et al., eds., New York, N.Y.: McGraw-Hill, pages 4433-4453, 2001). The contribution of this reaction to hemostasis is uncertain as fXII deficiency, unlike fXI deficiency, is not associated with abnormal bleeding in any species in which it has been identified (Gailani and Broze, *Metabolic and Molecular Basis of Inherited Disease*, Scriver et al., eds., New York, N.Y.: McGraw-Hill, pages 4433-4453, 2001). This is a key piece of supporting evidence for hypotheses proposing that fXI is either activated during hemostasis by a protease distinct from fXIIa, or that auxiliary mechanisms for fXI activation can compensate for the absence of fXIIa (Broze et al., *Biochemistry* 29:7539-7546, 1990; Davie et al., *Biochemistry* 30:10363-10370, 1991; Renne et al., *Expert Rev. Cardiovasc. Ther.* 5:733-741, 2007).

In addition to fXIIa, other candidates for fXI activators include α-thrombin (Naito et al., *J. Biol. Chem.* 266:7353-7358, 1991; Gailani et al., *Science* 253:909-912, 1991), meizothrombin (von dem Borne et al., *Thromb. Haemost.* 78:834-839, 1997), and fXIa (autoactivation) (Naito et al., *J. Biol. Chem.* 266:7353-7358, 1991; Gailani et al., *Science* 253:909-912, 1991). Thrombin has received much attention in this regard. Work from several laboratories supports a model in which thrombin or another protease generated early in coagulation activates fXI (von dem Borne et al., *Thromb. Haemost.* 78:834-839, 1997; von dem Borne et al., *Blood* 86:3035-3042, 1995; von dem Borne et al., *J. Clin. Invest.* 99:2323-2327, 1997; Cawthern et al., *Blood* 91:4581-4592, 1998; Keularts et al., *Thromb. Haemost.* 85:1060-1065, 2001; Oliver et al., *Arterioscler. Thromb. Vasc. Biol.* 19:170-177, 1999; Wielders et al., *Arterioscler. Thromb. Vasc. Biol.* 24:1138-1142, 2004), with fXIa then sustaining coagulation. This hypothesis has been challenged by a study that did not find evidence for fXI activation in thrombin or tissue factor (TF) stimulated plasma in the absence of fXII (Pedicord et al., *Proc. Natl. Acad. Sci. U.S.A.* 104:12855-12860, 2007). This work also showed that the process of collecting and preparing plasma can generate fXIa, giving the false impression in subsequent assays that fXIIa-independent fXI activation has occurred. These observations have been presented in support of a hypothesis, proposed previously by other investigators (Brunnée et al., *Blood* 81:580-586, 1993), that normal hemostasis in fXII deficiency reflects loss of fXIIa-initiated processes, such as fibrinolysis, that negate the propensity to bleed from simultaneous loss of fXI activation (Pedicord et al., *Proc. Natl. Acad. Sci. U.S.A.* 104:12855-12860, 2007; Blat et al., *Thromb. Haemost.* 99:457-460, 2008).

Coagulation factor XII (fXII) has long been considered a potential target of safe antithrombotic therapy. However, no sufficiently potent inhibitor for fXII activity, such as a potent and useful antibody, has yet been identified. A small molecule fXIa inhibitor has been previously described; however, this irreversible enzyme inhibitor blocks both fXIa and plasma kallikrein (Schumacher et al., *Eur. J. Pharmacol.* 570(1-3): 167-174, 2007). Thus, a need exists for a potent, universal and specific inhibitor of fXI.

SUMMARY

Described herein are monoclonal antibodies, or antigen-binding fragments thereof, that are specific for coagulation factor XI (fXI) and universally recognize fXI from numerous mammalian species. The disclosed antibodies prevent fXI activation by fXIIa, but do not interfere with thrombin- or tissue factor-mediated activation of fXI, which is important for the maintenance of hemostasis.

In some embodiments, the fXI-specific monoclonal antibodies or antigen-binding fragments thereof, have a variable light ($V_L$) chain with an amino acid sequence including at least a portion of SEQ ID NO: 1, such as one or more complementarity determining regions (CDRs), and/or a variable heavy ($V_H$) chain with an amino acid sequence including at least a portion of SEQ ID NO: 3, such as one or more CDRs. The antibodies contemplated herein also include any fXI-specific monoclonal antibodies or antigen-binding fragments thereof, that are competitive inhibitors with such antibodies for binding to fXI. In specific examples, the monoclonal antibodies include a $V_L$ with an amino acid sequence comprising SEQ ID NO: 1 and a $V_H$ with an amino acid sequence comprising SEQ ID NO: 3.

Also provided herein are immunoconjugates comprising the fXI-specific antibodies and a fusion partner, such as an effector molecule, a label or a heterologous polypeptide, as well as compositions comprising the antibodies and immunoconjugates. Further provided are isolated nucleic acid molecules encoding the antibodies and immunoconjugates disclosed herein, vectors comprising the isolated nucleic acid molecules and isolated host cells transduced by the vectors.

Further provided is a method of inhibiting activation of fXI by fXIIa in a subject by selecting a subject in need of treatment and administering to the subject an inhibitory amount of a fXI-specific antibody disclosed herein, or an immunoconjugate or composition thereof. In some embodiments, the subject in need of treatment is a subject has or is at risk of developing thrombosis, or is a subject with pathological activation of fXI.

The foregoing and other objects, features, and advantages of the invention will become more apparent from the following detailed description, which proceeds with reference to the accompanying figures.

BRIEF DESCRIPTION OF THE DRAWINGS

FIGS. 1A-1E are graphs showing the effect of fXI on thrombin generation in fXI-deficient plasma. Thrombin generation in plasma is shown as area under the curve (AUC) for FIG. 1A and FIG. 1B, or thrombin generation over time for FIGS. 1C-1E. Coagulation was initiated with (A) $Ca^{2+}$ and varying concentrations of TF in the presence (white bars) or absence (black bars) of fXI; (B) 0.23 pM TF and $Ca^{2+}$ (white bars) or $Ca^{2+}$ alone (black bars) at varying fXI concentrations; (C) $Ca^{2+}$ and 1.6 pM (curves 1 and 2) or 0.23 pM (curves 3 and 4) TF in the presence (curves 1 and 3) or absence (curves 2 and 4) of fXI; (D) $Ca^{2+}$ and 30 pM (curves 1 and 2) or 6 pM (curves 3 and 4) fXa, in the presence (curves 1 and 3) or absence (curves 2 and 4) of fXI; or (E) 5 nM α-thrombin in the presence (curve 1) or absence (curve 2) of fXIa.

FIGS. 3A-3C are graphs showing the effect of recombinant fXI-Ala$^{83-84}$ on thrombin generation in fXI-deficient plasma. (A) Activation of 25 nM $fXI^{WT}$ (white squares and white circles) or fXI-Ala$^{83-84}$ (black squares and black circles) by 5 nM fXIIa (white and black squares) or 15 nM α-thrombin (white and black circles). fXIa generation was followed by cleavage of S2366. (B and C) Thrombin generation in fXI-deficient plasma with (B) phospholipids or (C) gel-purified platelets and recombinant (1) $fXI^{WT}$, (2) vehicle, or (3) DU-Ala$^{83-83}$.

FIGS. 5A-5C are immunoblots using anti-factor XI monoclonal antibodies and a graph showing the effect of fXI antibodies on fXI activation. Western blots of recombinant fXI and PK using (A) anti-human fXI IgG O1A6 or (B) anti-murine fXI IgG 14E11 as primary antibody. Abbreviations at the tops of the blots indicate human fXI (H); murine fXI (M); human fXI with either the human prekallikrein A1, A2, A3, or A4 domains; and human prekallikrein (PK). Note that fXI/PKA4 is approximately half the molecular mass of other fXI species. This is because the PK A4 domain cannot mediate dimer formation. Positions of molecular mass standards are sown at the left of panel A. (C) Activation of 25 nM fXI with 5 nM fXIIa (white and black circles) or 15 nM α-thrombin (white squares and triangles) in the presence (black circles and white triangles) or absence (white circles and squares) of 100 nM IgG 14E11. fXIa generation was followed by cleavage of S2366.

FIGS. 7A and 7B are graphs showing the effects of anti-fXI IgG O1A6 and 14E11 on thrombin generation in fXII-deficient plasma induced to clot with α-thrombin or fXIIa. (A) Thrombin generation in fXII-deficient plasma induced to clot with $Ca^{2+}$ and 5 nM α-thrombin (curves 1-3) or vehicle (curve 4). Thrombin generation in curve 2 is in the presence of 50 nM anti-fXI IgG O1A6 and curve 3 in the presence of 50 nM anti-fXI 14E11. (B) Thrombin generation in fXII-deficient plasma induced to clot with $Ca^{2+}$ and 1 nM fXIIa in the presence of (1) vehicle, (2) 50 µg/mlCTI, or (3) 50 nM anti-fXI IgG 14E11.

Sequence Listing

Figures 2A, 2B:
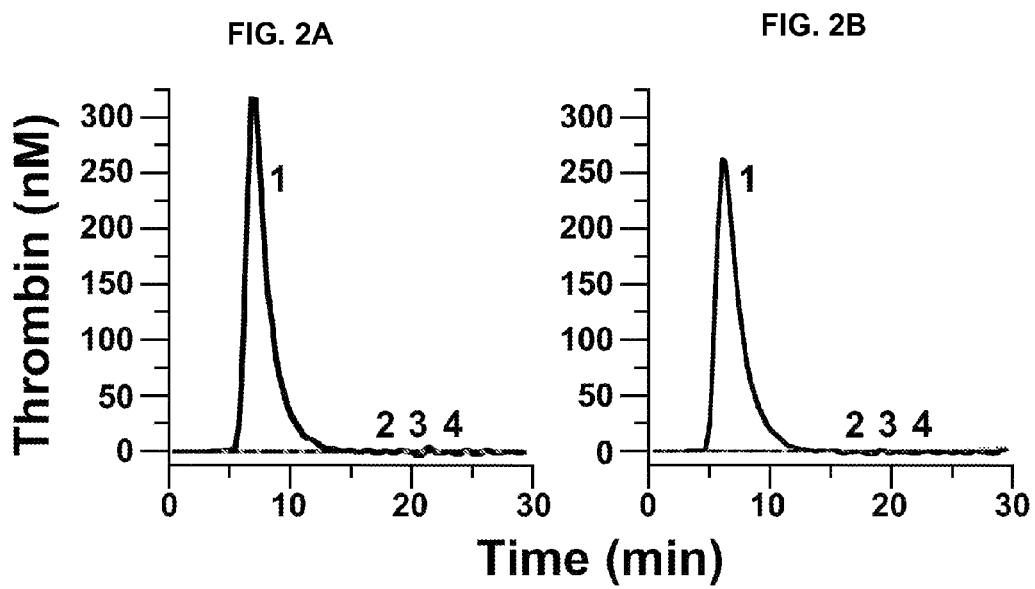
FIGS. 2A and 2B are graphs showing the effect of recombinant fXI on thrombin generation in fXI-deficient plasma. Shown is thrombin generation in fXI-deficient plasma with (A) phospholipids or (B) gel-purified platelets and recombinant (1) $fXI^{WT}$, (2) vehicle, (3) DU-Ala$^{557}$, or (4) fXI-Ala$^{195-197}$.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 15, 2013, 4.08 KB, which is incorporated by reference herein. In the accompanying sequence listing:

SEQ ID NO: 1 is the amino acid sequence of the $V_L$ of 14E11.

SEQ ID NO: 2 is the nucleotide sequence of the $V_L$ of 14E11 (and encodes SEQ ID NO: 1).

SEQ ID NO: 3 is the amino acid sequence of the $V_H$ of 14E11.

SEQ ID NO: 4 is the nucleotide sequence of the $V_H$ of 14E11 (and encodes SEQ ID NO: 3).

DETAILED DESCRIPTION

I. Introduction

Coagulation factor XII (fXII) has recently been considered a potential target of safe antithrombotic therapy (Renné et al., *J Exp Med.* 202(2):271-81, 2005; Kleinschnitz et al., *J Exp Med.* 203(3):513-8, 2006). However, no sufficiently potent inhibitor for fXII activity, such as a potent and useful antibody, has yet been identified. One of the potential reasons for the failure is that fXII is an abundant protein in blood, and when activated, is converted into a very active enzyme that is difficult to block in vivo.

Disclosed herein is the identification of an antibody that targets the procoagulant substrate of activated fXII (fXIIa). Targeting the substrate instead of the enzyme is beneficial because the concentration of the coagulant substrate, factor XI (fXI), is significantly lower than the concentration of fXII. Moreover, it is useful to target the substrate (fXI) rather than the enzyme (fXIIa), because this approach provides unparalleled treatment specificity and leaves other, potentially beneficial biological activities of fXIIa, such as activation of prekallikrein (and thus production of bradykinin), intact. Substrate targeting results in the very specific pharmacodynamic effect of exclusive anticoagulant activity, by inhibition of the procoagulant activity of the contact activation complex and therefore the intrinsic coagulation cascade.

Coagulation factor XI is thought to contribute to thrombosis, a pathological condition that, depending on its anatomical localization, results in high mortality diseases, including the leading causes of death (such as myocardial infarction, ischemic stroke, pulmonary thrombo-embolism, disseminated intravascular coagulation (DIC) and severe systemic inflammatory response syndrome (SSIRS) in infections and other conditions). fXI is a proenzyme (zymogen) that can be activated by at least three other enzymes, factor XIIa (fXIIa), thrombin (IIa), and factor XIa (fXIa). Activated factor XI (fXIa) then activates factor IX (fIX) and ultimately amplifies thrombin generation.

Disclosed herein is the identification and characterization of a monoclonal antibody (14E11) specific for fXI. 14E11 is a murine monoclonal $IgG_2$ antibody that binds to the A2 domain of fXI and inhibits its activation by fXIIa. The antibody does not block activation of fXI by thrombin or tissue factor, or activation of prekallikrein by fXIIa, nor does it block the activity of fXIa. The findings disclosed herein indicate that it is possible to target fXIIa-mediated activation of fXI, which promotes thrombus growth, without interfering with thrombin-mediated activation of fXI that is important for hemostasis.

In particular, described herein is the finding that 14E11 prolongs the activated partial thromboplastin time (APTT) of all tested mammalian plasmas, including mouse, human, baboon, and others. This illustrates that 14E11 (and binding fragments thereof, as well as monoclonal antibodies that bind competitively with 14E11) are potent antithrombotic agents. In addition, the studies described herein reveal that 14E11 is antithrombotic in a mouse model of acute arterial thrombosis, and that it inhibits thrombus formation in a primate model of thrombosis.

Accordingly, the fXI-specific antibodies of the present disclosure are safe for the treatment of thrombotic diseases where activation of fXI by fXIIa has a pathogenic role. Since hemostatic fXI activation and beneficial FXIIa activities are not be affected by this antibody, this antibody represents a monospecific anticoagulant that has no hemorrhagic (hemostasis impairment) or other FXIIa-dependent side effect. It is therefore different from other fXI inhibitors that block both the prothrombotic (negative, harmful effect) and prohemostatic (positive, beneficial effect) of fXI. It is also different from direct FXIIa inhibitors that block both beneficial (physiological) and harmful (pathological) activities of FXIIa.

II. Abbreviations

APTT Activated partial thromboplastin time
AUC Area under the curve
BSA Bovine serum albumin
CAT Calibrated automated thrombography
CTI Corn-trypsin-inhibitor
DFP Diisopropylfluorophosphate
DIC Disseminated intravascular coagulation
ETP Endogenous thrombin potential
fIX Factor IX
fXI Factor XI
fXIa Activated factor XI
fXII Factor XII
fXIIa Activated factor XII
IC Inhibitory concentration
Ig Immunoglobulin
PK Prekallikrein
PRP Platelet-rich plasma
PTT Partial thromboplastin time
RBC Rabbit brain cephalin
SDS Sodium dodecyl sulfate
SSIRS Severe systemic inflammatory response syndrome
TF Tissue factor
tPA Tissue plasminogen activator
$V_H$ Variable heavy chain
$V_L$ Variable light chain III. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: The introduction of a composition into a subject by a chosen route. For example, if the chosen route is intravenous, the composition is administered by introducing the composition into a vein of the subject.

Animal: Living multi-cellular vertebrate organisms, a category that includes, for example, any mammal. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, such as fXI or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies) and heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds fXI will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies. As used herein "monoclonal antibodies" further includes antigen-binding fragments, such as Fv, scFv, dsFv or Fab fragments.

A "chimeric antibody" has framework residues from one species, such as human, and CDRs (which generally confer antigen binding) from another species, such as a murine antibody that specifically binds fXI.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Anticoagulant: A compound (such as a pharmaceutical agent or molecule) that prevents or inhibits the clotting of blood. Pharmaceutical anticoagulants can be used to treat thrombotic disorders, such as deep vein thrombosis, pulmonary embolism, myocardial infarction and stroke.

Antigen-binding fragment: As used herein, an antigen-binding fragment of a monoclonal antibody is a portion of a monoclonal antibody that retains its ability to specifically bind the antigen against which the monoclonal antibody was raised. Antigen-binding fragments, include but are not limited to Fab fragments, Fab' fragments, F(ab)'$_2$ fragments, single chain Fv proteins, and disulfide stabilized Fv proteins.

Antithrombotic: Any compound (such as a pharmaceutical agent or molecule) that prevents or inhibits formation of a thrombus. Antithrombotic agents include anticoagulants (which limit the ability of platelets to clot), antiplatelet drugs (which limit the migration and aggregation of platelets) and thrombolytic drugs (which dissolve clots after they have formed).

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, a high binding affinity is measured by a competition radioimmunoassay. In another embodiment, binding affinity is measured by ELISA.

Bleeding disorder: Refers to any congenital, acquired or induced defect that results in abnormal (or pathological) bleeding. Examples include, but are not limited to, disorders of insufficient clotting or hemostasis, such as hemophilia A (a deficiency in Factor VIII), hemophilia B (a deficiency in Factor IX), hemophilia C (a deficiency in Factor XI), other clotting factor deficiencies (such as Factor VII or Factor XIII), abnormal levels of clotting factor inhibitors, platelet disorders, thrombocytopenia, vitamin K deficiency and von Willebrand's disease.

Coagulation: The process of polymerization of fibrin monomers, resulting in the transformation of blood or plasma from a liquid to a gel phase. Coagulation of liquid blood may occur in vitro, intravascularly or at an exposed and injured tissue surface. In vitro blood coagulation results in a gelled blood that maintains the cellular and other blood components in essentially the same relative proportions as found in non-coagulated blood, except for a reduction in fibrinogen content and a corresponding increase in fibrin.

Competitive inhibitor: Any molecule that completes with another molecule for binding to a substrate (such as an antigen). Methods of identifying molecules that are competitive inhibitors are well known in the art (for example, competitive binding assays).

Conservative variants: "Conservative" amino acid substitutions are those substitutions that do not substantially affect or decrease the affinity of an antibody to fXI. For example, an antibody that specifically binds fXI can include at most about 1, at most about 2, at most about 5, and most about 10, or at most about 15 conservative substitutions and specifically bind the fXI polypeptide. The term conservative variation also includes the use of a substituted amino acid in place of an unsubstituted parent amino acid, provided that antibody specifically binds fXI. Non-conservative substitutions are those that reduce an activity or binding to fXI.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Domain: A protein structure which retains its tertiary structure independently of the remainder of the protein. In some cases, domains have discrete functional properties and can be added, removed or transferred to another protein without a loss of function.

Effector molecule (EM): The portion of a chimeric molecule that is intended to have a desired effect on a cell or system or substance to which the chimeric molecule is targeted. The term effector molecule is interchangeable with effector moiety, therapeutic agent, diagnostic agent, and similar terms.

Therapeutic agents include such compounds as nucleic acids, proteins (including monoclonal antibodies and antigen-binding fragments of monoclonal antibodies), peptides, amino acids or derivatives, glycoproteins, radioisotopes, lipids, carbohydrates, recombinant viruses or toxins. Nucleic acid therapeutic and diagnostic moieties include antisense nucleic acids, derivatized oligonucleotides for covalent cross-linking with single or duplex DNA, and triplex forming oligonucleotides. Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, and enzymes.

Epitope: An antigenic determinant. These are particular chemical groups or peptide sequences on a molecule that are antigenic, i.e. that elicit a specific cellular immune response. An antibody specifically binds a particular antigenic epitope on a polypeptide, such as fXI.

Factor XI (fXI): fXI is the zymogen form of activated factor XI (fXIa), an enzyme involved in coagulation. This protein is found only in mammals. fXI is activated by fXIIa, thrombin and via an autocatalytic mechanism (see FIG. 8). fXI is synthesized as a single polypeptide chain, but circulates as a homodimer formed by disulfide bonds. Each polypeptide chain of fXI is approximately 80 kD. During activation of factor XI, an internal peptide bond is cleaved by factor XIIa in each of the two chains, resulting in activated factor XIa, a serine protease composed of two heavy and two light chains held together by disulfide bonds. Activated f XI triggers the middle phase of the intrinsic pathway of blood coagulation by activating factor IX. Defects in this factor lead to Rosenthal syndrome (also known as hemophilia C), a blood coagulation abnormality. The fXI protein is encoded by the F11 gene. fXI is also known as coagulation factor XI or plasma thromboplastin antecedent. As used herein, "coagulation factor XI," "factor XI" or "fXI" refers to any fXI from any mammalian species that expresses the protein. For example, fXI can be human, non-human primate (such as baboon), mouse, dog, cat, cow, horse, pig, rabbit, raccoon, tiger, anteater, elephant (such as African elephant or Asian elephant), or llama.

Framework region: Amino acid sequences interposed between CDRs (or hypervariable regions). Framework regions include variable light and variable heavy framework regions. Each variable domain comprises four framework regions, often referred to as FR1, FR2, FR3 and FR4. The framework regions serve to hold the CDRs in an appropriate orientation for antigen binding. Framework regions typically form β-sheet structures.

Fusion partner: Refers to any molecule that is fused (such as covalently linked) to another molecule. In the context of the present disclosure, an immunoconjugate includes an antibody linked to a fusion partner. In some examples, the fusion partner is an effector molecule, a label (such as a detectable label), a heterologous polypeptide or a drug.

Hemostasis: Refers to the physiologic process whereby bleeding is halted. Hemostatic agents are those that prevent, treat or ameliorate abnormal bleeding, such as abnormal bleeding caused by a bleeding disorder or bleeding episode. Disorders of hemostasis include, for example, platelet disorders, such as idiopathic thrombocytopenic purpura, and disorders of coagulation, such as hemophilia. Hemostasis can also refer to the complex interaction between vessels, platelets, coagulation factors, coagulation inhibitors and fibrinolytic proteins to maintain the blood within the vascular compartment in a fluid state. The objective of the hemostatic system is to preserve intravascular integrity by achieving a balance between hemorrhage and thrombosis. As used herein, "promoting hemostasis" refers to the process of contributing to or improving hemostasis in a subject. For example, an agent that promotes hemostasis can be an agent that reduces abnormal bleeding, such as by halting bleeding more rapidly, or by reducing the amount of blood loss.

Heterologous: A heterologous polypeptide or polynucleotide refers to a polypeptide or polynucleotide derived from a different source or species. For example, an immunoconjugate comprising a heterologous polypeptide refers to a fusion protein in which an antibody (or a portion of an antibody) is linked to a different polypeptide, such as a marker protein.

Immunoconjugate: A covalent linkage of a fusion partner, such as an effector molecule, label, heterologous polypeptide or other moiety, to an antibody or antigen binding fragment thereof. The linkage can be by chemical or recombinant means, for instance. In some cases, the linkage is chemical, wherein a reaction between the antibody moiety and the fusion partner has produced a covalent bond formed between the two molecules to form one molecule. A peptide linker (short peptide sequence) can optionally be included between the antibody and the effector molecule.

Inhibitory amount or inhibitory dose: Refers to the quantity of a specific substance sufficient to achieve inhibition of the activity of a particular molecule or inhibition of the activation of a particular molecule. For instance, this can be the amount necessary to inhibit activation of fXI in subject or a sample (such as a plasma or serum sample). In some embodiments, the inhibitory amount of a monoclonal antibody specific for fXI, or an antigen-binding fragment thereof, is the amount necessary to inhibit activation of fXI by at least 50%. In some examples, the inhibitor amount is the amount necessary to inhibit activation of fXI by 90-100%.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: "Linker" in some embodiments refers to a peptide serving to link a targeting moiety, such as an antibody, to a binding partner, such as a detectable label or heterologous polypeptide. In some cases, a linker is a peptide within an antibody binding fragment (such as an Fv fragment) which serves to indirectly bond the variable heavy chain to the variable light chain.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to a fusion partner. The linkage can be either by chemical or recombinant means. "Chemical means" refers to a reaction between the antibody moiety and the fusion partner such that there is a covalent bond formed between the two molecules to form one molecule.

Mammal: This term includes both human and non-human mammals. Similarly, the term "subject" includes both human and veterinary subjects.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Parenteral: Refers to administration other than through the alimentary canal (the digestive tract), such as by subcutaneous, intramuscular, intrasternal or intravenous administration.

Pathological activation: As used herein, "pathological activation of fXI" refers to the undesired or abnormal activation of fXI which can result in harmful effects (such as the promotion of thrombosis) to a subject exhibiting such pathological activation.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease, such as cancer.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50%, such as at least 60%, at least 70%, at least 80%, at least 90%, at least 95%, or at least 98%, of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a fXI polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a fXI specific binding agent is an agent that binds substantially to a fXI polypeptide, but not to other molecules. In one embodiment, the specific binding agent is a monoclonal antibody that specifically binds the fXI polypeptide.

The term "specifically binds" refers, with respect to an antigen such as fXI, to the preferential association of an antibody or other ligand, in whole or part, with a cell or tissue bearing that antigen and not to cells or tissues lacking that antigen. It is recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the fXI polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals. In some embodiments, a subject is any mammal, such as a human, non-human primate or veterinary subject such as a dog.

Therapeutically effective amount: A quantity of a specific substance sufficient to achieve a desired effect in a subject being treated. For instance, this can be the amount necessary to inhibit activation of fXI. When administered to a subject, a dosage will generally be used that will achieve target tissue concentrations that has been shown to achieve a desired in vitro effect.

Thrombosis: The formation or presence of a clot (also called a "thrombus") inside a blood vessel, obstructing the flow of blood through the circulatory system. Thrombosis is usually caused by abnormalities in the composition of the blood, quality of the vessel wall and/or nature of the blood flow. The formation of a clot is often caused by an injury to the vessel wall (such as from trauma or infection) and by the slowing or stagnation of blood flow past the point of injury. In some cases, abnormalities in coagulation cause thrombosis.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Monoclonal Antibodies Specific for Factor-XI

Described herein are monoclonal antibodies, and antigen-binding fragments thereof, that are specific for coagulation factor XI (fXI) and universally recognize fXI from numerous and diverse mammalian species. The disclosed antibodies prevent fXI activation by fXIIa, but do not significantly interfere with thrombin- or tissue factor-mediated activation of fXI, which is important for the maintenance of hemostasis. As a result, the disclosed antibodies are useful for inhibiting thrombosis without significantly altering hemostasis. As described herein, the disclosed anti-fXI monoclonal antibodies are capable of binding fXI from a number of different mammalian species, including, but not limited to, human, mouse, baboon, anteater, cow, horse, pig, rabbit, raccoon, tiger, cat, dog, African elephant and llama.

Thus, provided herein are isolated monoclonal antibodies, or antigen-binding fragments thereof, that specifically bind fXI and prevent activation of fXI by fXIIa. In some embodiments, the isolated monoclonal antibodies, or antigen-binding fragments thereof, include a $V_L$ comprising at least a portion of the amino acid sequence of SEQ ID NO: 1, such as one or more CDRs of SEQ ID NO: 1. In some embodiments, the isolated monoclonal antibodies, or antigen-binding fragments thereof, include a $V_H$ comprising at least a portion of the amino acid sequence of SEQ ID NO: 3, such as one or more CDRs of SEQ ID NO: 1. In some examples, the $V_L$ of the antibody or fragment comprises amino acids 24-34 (CDR1), 50-63 (CDR2), and/or 91-98 (CDR3) of SEQ ID NO: 1. In some examples, the $V_H$ of the antibody or fragment comprises amino acids 31-35 (CDR1), 50-68 (CDR2) and/or 98-105 (CDR3) of SEQ ID NO: 3. In some embodiments, the monoclonal antibodies or antigen-binding fragment thereof include sequence from both SEQ ID NO:1 and SEQ ID NO: 3. Further contemplated by the current disclosure are any fXI-specific antibodies that are competitive inhibitors of antibodies comprising portions of SEQ ID NO: 1 and/or SEQ ID NO: 3 for binding to fXI.

In some embodiments, the amino acid sequence of the $V_L$ is at least 80%, at least 85%, at least 90%, at least 95% or at least 99% identical to SEQ ID NO: 1. In other embodiments, the amino acid sequence of the $V_L$ comprises SEQ ID NO: 1 or consists of SEQ ID NO: 1.

In some embodiments, the amino acid sequence of the $V_H$ is at least 80%, at least 85%, at least 90%, at least 95% or at least 99% identical to SEQ ID NO: 3. In other embodiments, the amino acid sequence of the $V_H$ comprises SEQ ID NO: 3 or consists of SEQ ID NO: 3.

In particular examples, the isolated monoclonal antibody or antigen-binding fragment thereof includes a $V_L$ with an amino acid sequence comprising SEQ ID NO: 1 and a $V_H$ with an amino acid sequence comprising SEQ ID NO: 3.

The disclosed fXI-specific antibodies can be, for example, murine antibodies, chimeric antibodies (e.g., having both murine and human sequences), humanized antibodies or fully human antibodies. In particular examples, the antibodies are humanized antibodies.

The fXI-specific monoclonal antibodies or antigen-binding fragments of the current disclosure can be any isotype, including IgG, IgM, IgE, IgD or IgA. The antibodies can further be any subtype. For example, IgG antibodies include subtypes $IgG_1$, $IgG_2$ (including $IgG_{2a}$ and $IgG_{2b}$), $IgG_3$ and $IgG_4$. The class of an antibody that specifically binds fXI can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds fXI that was originally IgG may be class switched to an IgM. Class switching can also be used to convert one IgG subclass to another, such as from $IgG_1$ to $IgG_2$.

Antibody fragments are encompassed by the present disclosure, such as Fab, F(ab')$_2$, and Fv which include a heavy chain and light chain variable region and are capable of binding the epitopic determinant on fXI. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), defined as a genetically engineered molecule containing the variable region of the light chain, the variable region of the heavy chain, linked by a suitable polypeptide linker as a genetically fused single chain molecule; and (6) A dimer of a single chain antibody (scFV$_2$), defined as a dimer of a scFV. This has also been termed a "minianti-body."

Methods of making these fragments are known in the art (see for example, Harlow and Lane, *Antibodies: A Laboratory Manual*, Cold Spring Harbor Laboratory, New York, 1988).

In a further group of embodiments, the antibodies are Fv antibodies, which are typically about 25 kDa and contain a complete antigen-binding site with three CDRs in each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art.

Further provided herein are compositions comprising one or more of the provided monoclonal antibodies, or one or more antigen-binding fragments thereof, and a pharmaceutically acceptable carrier. Nucleic acids encoding these antibodies, expression vectors comprising these nucleic acids, and isolated host cells that express the nucleic acids are also provided. The compositions, nucleic acid molecules, vectors and host cells are described in greater detail below.

Also described herein are immunoconjugates comprising the monoclonal antibodies specific for fXI. The immunoconjugates comprise an antibody and a fusion partner. The fusion partner can be any therapeutic agent, detectable label or other moiety. Compositions comprising the immunoconjugates are also described. Immunoconjugates of the current disclosure are discussed in greater detail below.

Compositions comprising the monoclonal antibodies specific for fXI can be used for research, diagnostic and/or therapeutic purposes. For example, the monoclonal antibodies can be used to treat thrombosis or any condition associated with pathological activation of fXI. Methods of use of the disclosed fXI-specific monoclonal antibodies and antigen-binding fragments thereof are described in detail below.

A method of inhibiting activation of fXI by factor XIIa (fXIIa) in a subject is also provided. The method comprises (a) selecting a subject in need of treatment; and (b) administering to the subject an inhibitory amount of a monoclonal antibody, immunoconjugate or the composition disclosed herein. In some embodiments, the subject in need of treatment has or is at risk of developing thrombosis. In some embodiments, the subject in need of treatment is a subject suffering from or at risk of suffering from myocardial infarction, ischemic stroke, pulmonary thrombo-embolism, disseminated intravascular coagulation, severe systemic inflammatory response syndrome, metastatic cancer, or an infectious disease. In some embodiments, the subject in need of treatment is a subject with pathological activation of fXI. In some embodiments, the inhibitory amount of the monoclonal antibody, immunoconjugate or composition is an amount sufficient to inhibit activation of fXI by at least 50%, at least 60%, at least 70%, at least 80%, at least 90%, at least 95%, at least 99% or 100%. In particular examples, the inhibitory amount of the monoclonal antibody, immunoconjugate or composition is an amount sufficient to inhibit activation of fXI by 90-100%. The antibody, immunoconjugate or composition can be administered using any suitable route of administration, and any suitable dose or dosing schedule, discussed in greater detail in the sections below.

A method of purifying fXI from a biological sample by contacting the sample with a monoclonal antibody, or antigen-binding fragment thereof, disclosed herein is also provided. For example, the fXI-specific antibodies of the disclosure can be used to immunoprecipitate fXI from any biological sample of any mammalian species. Methods of immunoprecipitation are well known in the art. In some examples, the fXI-specific antibody is conjugated to a bead, such as a magnetic bead that allows for efficient separation of antibody bound to antigen (e.g., fXI bound to a fXI-specific antibody). The biological sample can be any sample where fXI protein is found. In some examples, the biological sample is a fluid sample, such as a blood, serum or plasma sample, or a tissue sample.

Further provided is a diagnostic method of detecting fXI in a biological sample, or measuring the level of fXI in a biological sample. In some examples, the biological sample is a fluid sample, such as a blood, serum or plasma sample, or a tissue sample. Methods of detecting proteins in a biological sample, or measuring the level of a protein in a biological sample, are well known in the art.

V. Factor XI and the Coagulation Cascade

Human factor XI (fXI) is synthesized as a single polypeptide, but circulates as a two-chain glycoprotein with a molecular weight of approximately 160 kD. The two chains are identical disulfide bonded polypeptides with molecular weights of approximately 80 kD. fXI is the zymogen form of activated factor XI (fXIa). fXI is activated to factor XIa by factor XIIa, by thrombin or via an autocatalytic mechanism (see FIG. 8). In humans, the gene for fXI (F11) is located at the distal end of chromosome 4 (4q35.2) and contains 15 exons spread over approximately 25 kb of genomic DNA (Asaki et al., *Biochemistry* 26:7221-7228, 1987; Kato et al., *Cytogenet. Cell Genet.* 52:77, 1989).

The cleavage site for the activation of factor XI by factor XIIa is an internal peptide bond between Arg-369 and Ile-370 in each polypeptide chain (Fujikawa et al., *Biochemistry* 25:2417-2424, 1986). Each heavy chain of factor XIa (369 amino acids) contains four tandem repeats of 90-91 amino acids called apple domains (designated A1-A4) plus a short connecting peptide (Fujikawa et al., Biochemistry 25:2417-2424, 1986; Sun et al., *J. Biol. Chem.* 274:36373-36378, 1999). The light chains of fXIa (each 238 amino acids) contain the catalytic portion of the enzyme with sequences that are typical of the trypsin family of serine proteases (Fujikawa et al., *Biochemistry* 25:2417-2424, 1986). Activated fXI triggers the middle phase of the intrinsic pathway of blood coagulation by activating factor IX. Individuals having defects in fXI develop hemophilia C (also known as Rosenthal syndrome), a blood coagulation abnormality.

During contact activation-initiated coagulation, factors XII, XI and IX are activated in sequence, promoting thrombin generation (Gailani and Broze, *Metabolic and Molecular Basis of Inherited Disease*, Scriver et al., eds., New York, N.Y.: McGraw-Hill, pages 4433-4453, 2001). The different bleeding diatheses associated with deficiencies of these proteins, however, indicate the situation in vivo is more complex. Factor VIIa/TF also activates factor IX (Broze et al., *Biochemistry* 29:7539-46, 1990; Davie et al., *Biochemistry* 30:10363-10370, 1991; Osterud et al., *Proc. Natl. Acad. Sci. U.S.A.* 74:5260-5264, 1977) explaining the more severe bleeding in fIX deficiency relative to fXI deficiency. Similarly, fXI activation by a protease other than fXIIa can explain the different phenotypes of fXI and fXII deficiency. A significant body of prior work supports a model in which fXI contributes to coagulation in the absence of fXII (von dem Borne et al., *Thromb. Haemost.* 78:834-839, 1997; von dem Borne et al., *Blood* 86:3035-3042, 1995; von dem Borne et al., *J. Clin. Invest.* 99:2323-2327, 1997; Cawthern et al., *Blood* 91:4581-4592, 1998; Keularts et al., *Thromb. Haemost.* 85:1060-1065, 2001; Oliver et al., *Arterioscler. Thromb. Vasc. Biol.* 19:170-177, 1999; Wielders et al., *Arterioscler. Thromb. Vasc. Biol.* 24:1138-1142, 2004). Thrombin has been considered the likely fXIa-activating protease in these studies, based on results from purified protein systems (Naito et al., *J. Biol. Chem.* 266:7353-7358, 1991; Gailani et al., *Science* 253:909-912, 1991). Recently, Pedicord et al. examined fXI activation in plasma using an assay that measures complexes of the serpin C1 inhibitor (C1-NH) and fXIa (lower limit of detection approximately 5 pM fXIa) (Pedicord et al., *Proc. Natl. Acad. Sci. U.S.A.* 104:12855-12860, 2007). fXIa generation was not detected after addition of thrombin or TF to plasma containing the fXIIa inhibitor CTI. In the studies described in the examples below, plasma was prepared from blood collected directly into CTI. Omitting CTI during collection resulted in fXI activation, likely during phlebotomy or plasma preparation. Consistent with this, a fXI antibody inhibited an indicator of coagulation activity (chromogenic substrate cleavage) only in plasma prepared in the absence of CTI. It was postulated that studies examining fXI activation in the absence of fXII may not have taken sufficient steps to account for fXIa formed during plasma preparation, leading to the erroneous conclusion that fXIa was generated in a fXII-independent manner after initiation of coagulation by TF or thrombin.

von dem Borne et al. first demonstrated that fibrin formation and resistance to fibrinolysis depend on fXI in plasma induced to clot with low concentrations of thrombin or TF (von dem Borne et al., *Blood* 86:3035-3042, 1995). Only about 1 pM fXIa was required to protect clots from fibrinolysis, a value below the detection limit of the assay used by Pedicord et al. This study used fXII-deficient plasma that was subsequently depleted of fXI, and included an evaluation of fXIa in fXI preparations. It was determined that fXIa contamination was insufficient to explain the anti-fibrinolytic effect of fXI. It was also shown that a stable form of the thrombin precursor meizothrombin promoted fXI-dependent resistance to fibrinolysis, consistent with fXI activation by a product of prothrombin activation (von dem Borne et al., *Thromb. Haemost.* 78:834-839, 1997). Cawthern et al. confirmed that fXI had a positive effect on markers of thrombin generation at 5 pM TF in whole blood (Cawthern et al., *Blood* 91:4581-4592, 1998), and Keularts et al. used a thrombin generation assay to directly demonstrate the fXI-dependence of thrombin generation in plasma stimulated with approximately 2 pM TF (Keularts et al., *Thromb. Haemost.* 85:1060-1065, 2001). While it is difficult to determine which protease was responsible for fXI activation in these studies, thrombin was considered the most likely candidate.

The studies described in the examples below employed two plasma systems designed to address the concern of fXIa contamination by avoiding exposure of fXI to fXIIa. The first system used fXI-deficient plasma supplemented with CTI, to which DFP-treated fXI was added, whereas the second system used fXII-deficient plasma in which endogenous fXI has never been exposed to fXIIa. Results with both systems showed that fXI is required for thrombin generation in recalcified plasma stimulated with low concentrations of TF, fXa, or α-thrombin. Recalcification in the absence of TF, fXa or α-thrombin did not support thrombin generation, indicating contaminating fXIa was below a threshold for initiating the process. The sensitivity of the assay to fXIa was also tested. In fXI-deficient plasma, 3 pM fXIa promoted thrombin generation weakly and inconsistently. In contrast, in plasma containing fXI, thrombin generation was consistently initiated by 0.3 pM fXIa. If the latter result was due to contamination of fXI with sufficient fXIa to promote thrombin generation (presumably >3 pM), the 0.3 pM fXIa trigger should not have been necessary, and recalcification alone should have promoted thrombin generation. This was not observed. That a fraction of the amount of fXIa needed to trigger thrombin generation in the absence of fXI, induced thrombin generation in its presence, strongly indicates fXIa is generated from endogenous fXI after addition of fXIa.

The hypothesis that a feedback loop involving thrombin activation of fXI was required for activation of factor IX was also tested, using recombinant fXI variants. In thrombin- or TF-stimulated plasma, fXIa activation of factor IX is required, as blocking the factor IX-binding exosite on the fXIa A3 domain with an antibody, or disrupting it with point mutations (Sun et al., *J. Biol. Chem.* 274:36373-36378, 1999), prevented thrombin generation. Furthermore, a fXI variant that is activated slowly by thrombin, supported thrombin generation poorly. This variant, fXI-Ala$^{83-84}$, has normal activity in contact activation-initiated clotting assays indicating it is activated reasonably well by fXIIa in a plasma environment, and subsequently activates factor IX.

Previous studies suggested that activated platelets enhance fXI activation by thrombin (Baglia et al., *Biochemistry* 37:2271-2281, 1998), although subsequent work has not confirmed this (Walsh, *Biochemistry* 46:12886-12887, 2007). In a system composed of purified coagulation factors, Oliver et al. observed that fXI activation, presumably by thrombin, was enhanced by platelets (Oliver et al., *Arterioscler. Thromb. Vasc. Biol.* 19:170-177, 1999). Wielders et al. showed that thrombin initiates and propagates thrombin generation in CTI-treated plasma only when platelets and fXI are present (Wielders et al., *Arterioscler. Thromb. Vasc. Biol.* 24:1138-1142, 2004).

While the data disclosed herein demonstrate a fXII-independent contribution of fXI to thrombin generation, it is also possible that fXIIa plays a role in fXI activation in either normal or pathologic coagulation. Indeed, recent studies with fXII-deficient mice suggest that a process involving the intrinsic pathway, possibly initiated by a contact activation-like process, contributes to arterial thrombus formation and central nervous system ischemia-reperfusion injury (Renne et al., *J. Exp. Med.* 202:271-281, 2005; Kleinschnitz et al., *J. Exp. Med.* 203:513-518, 2006).

Finally, it is illustrative to consider fXI activation from the perspective of vertebrate evolution. While fXI is found only in mammals, a gene for a protein that is clearly ancestral to fXI and the homologous protease prekallikrein (PK) first appears in amphibians (Ponczek et al., *J. Thromb. Haemost.* 6:1876-1883, 2008). All terrestrial non-mammalian vertebrates likely have this PK/fXI predecessor. fXII, which activates fXI and PK during contact activation, also first appears in amphibians (Ponczek et al., *J. Thromb. Haemost.* 6:1876-1883, 2008), and may well be an activator of the PK/fXI predecessor, retaining the capacity to activate fXI and PK after the gene duplication that produced these proteins from the predecessor. However, fXII expression has been lost at least twice during vertebrate evolution. Cetaceans (whales, porpoises, and dolphins), who share a common terrestrial ancestor, lack fXII (Robinson et al., *Science* 166:1420-1422, 1969). A point mutation in a common ancestor of these animals inactivated the fXII gene (Semba et al., *Thromb Res.* 90:31-37, 1998). Despite this, there is no evidence of deterioration of the fXI gene (Robinson et al., *Science* 166:1420-1422, 1969), indicating its product remains under selection pressure because it provides an adaptive function. Similarly, birds lack fXII (Ponczek et al., *J. Thromb. Haemost.* 6:1876-1883, 2008; Soulier et al., *Brit. J. Hematol.* 5:121-138, 1959; Frost et al., *Immunopharmacology* 45:75-81, 1999; Weir-M et al., *Thromb. Res.* 113:269-273, 2004), but have an intact gene for the PK/fXI predecessor (Ponczek et al., *J. Thromb. Haemost.* 6:1876-1883, 2008). In this case, there is convincing evidence that the fXII gene was lost during the lineage leading from reptiles to birds (Ponczek et al., *J. Thromb. Haemost.* 6:1876-1883, 2008). Thus, fXI and its predecessor can persist in the absence of fXII, supporting the conclusion that more than one protease can activate these proteins to allow them to fulfill their physiologic functions.

VI. fXI Antibody Polynucleotides and Polypeptides

Nucleic acid molecules (also referred to as polynucleotides) encoding the polypeptides provided herein (including, but not limited to antibodies, immunoconjugates and fusion proteins) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same fusion partner or antibody sequence. Thus, nucleic acids encoding antibodies, conjugates and fusion proteins are provided herein. In some embodiments, the nucleotide sequence of the light chain of the fXI-specific monoclonal antibody comprises SEQ ID NO: 2, or a portion thereof (such as a portion that encodes one or more CDRs). In some embodiments, the nucleotide sequence of the heavy chain of the fXI-specific monoclonal antibody comprises SEQ ID NO: 4, or a portion thereof (such as a portion that encodes one or more CDRs).

Nucleic acid sequences encoding the antibodies that specifically bind fXI can be prepared by any suitable method including, for example, cloning of appropriate sequences or by direct chemical synthesis. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding antibodies that specifically bind fXI can be prepared by cloning techniques. Examples of appropriate cloning and sequencing techniques, and instructions sufficient to direct persons of skill have been previously disclosed. Nucleic acids encoding anti-fXI antibodies can also be modified. Modification by site-directed mutagenesis is well known in the art. Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In some embodiments, an immunoconjugate is prepared by inserting the cDNA which encodes a fXI-specific monoclonal antibody into a vector which comprises the cDNA encoding the EM. The insertion is made so that the antibody and the EM are read in-frame, that is in one continuous polypeptide which contains a functional antibody region and a functional EM region. In one embodiment, cDNA encoding an EM, label or enzyme is ligated to an antibody so that the EM, label or enzyme is located at the carboxyl terminus of the antibody. In another embodiment, the EM, label or enzyme is located at the amino terminus of the antibody. In a another example, cDNA encoding the EM, label or enzyme is ligated to a heavy chain variable region of an antibody, so that the EM, label or enzyme is located at the carboxyl terminus of the heavy chain variable region. The heavy chain-variable region can subsequently be ligated to a light chain variable region of the antibody using disulfide bonds. In a yet another example, cDNA encoding an EM, label or enzyme is ligated to a light chain variable region of an antibody, so that the EM, label or enzyme is located at the carboxyl terminus of the light chain variable region. The light chain-variable region can subsequently be ligated to a heavy chain variable region of the antibody using disulfide bonds.

Once the nucleic acids encoding a fXI-specific antibody, or an immunoconjugate thereof, are isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as Cos, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated proteins described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the Cos, CHO, HeLa and myeloma cell lines.

Modifications can be made to a nucleic acid encoding a polypeptide described herein (i.e., a fXI-specific monoclonal antibody or an immunoconjugate comprising the antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or fusion partners can be purified according to standard procedures of the art, including ammonium sulfate precipitation, affinity columns, column chromatography, and the like (see, generally, R. Scopes, Protein Purification, Springer-Verlag, N.Y., 1982). The antibodies and immunoconjugates need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein (see, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989).

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al. (*Biochemistry* 9: 5015-5021, 1970), and especially as described by Buchner et al. (*Anal. Biochem.* 205:263-270, 1992).

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

VII. Antibody Conjugates and Fusion Proteins

Anti-fXI monoclonal antibodies, and antigen-binding fragments thereof, described herein can be recombinantly fused to a heterologous polypeptide at the N- or C-terminus or chemically conjugated (including covalent and non-covalent conjugations) to polypeptides or other compositions. The present disclosure contemplates antibody conjugates comprising a fXI-specific antibody or antibody fragment and any suitable fusion partner. For example, anti-factor XI monoclonal antibodies can be recombinantly fused or conjugated to molecules useful as labels in detection assays, or to fusion partners such as heterologous polypeptides, drugs, radionuclides, or toxins (see, e.g., PCT publication Nos. WO 92/08495; WO 91/14438; and WO 89/12624; U.S. Pat. No. 5,314,995; and EP 396,387 for general teachings related to making antibody-based fusion proteins). The present disclosure also encompasses fusion proteins comprising an anti-fXI antibody and a heterologous polypeptide. For example, the heterologous polypeptide to which the antibody is fused can be useful for function, or could increase the in vivo half life of the polypeptides, or could serve as a marker sequence that facilitates purification or detection.

Fusion proteins can be prepared using methods that are well known in the art (see, for example, U.S. Pat. Nos. 5,116, 964 and 5,225,538). The precise site at which the fusion is made can be selected empirically to optimize the binding characteristics of the fusion protein. DNA encoding the fusion protein is then transfected into a host cell for expression.

Anti-fXI monoclonal antibodies of the present disclosure can be used in non-conjugated form or can be conjugated to at least one of a variety of molecules, for example, to improve the therapeutic properties of the molecule, to facilitate target detection, or for imaging or therapy of a subject. In particular, anti-factor XI monoclonal antibodies can be conjugated to therapeutic agents, prodrugs, peptides, proteins, enzymes, viruses, lipids, biological response modifiers, pharmaceutical agents, or PEG.

Techniques for conjugating various moieties to an anti-factor XI antibody are well known. Both covalent and non-covalent attachment means may be used. The procedure for attaching a fusion partner to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the fusion partner. Alternatively, the antibody is derivatized to expose or attach additional reactive functional groups. The derivatization may involve attachment of any of a number of linker molecules. The linker can be any molecule used to join the antibody to the fusion partner. The linker is capable of forming covalent bonds to both the antibody and to the fusion partner. Suitable linkers are well known to those of skill in the art and include, but are not limited to, straight or branched-chain carbon linkers, heterocyclic carbon linkers, or peptide linkers. Where the antibody and the fusion partner are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the fusion partner from the antibody when the immunoconjugate has reached its target site. Therefore, in these circumstances, immunoconjugates will comprise linkages that are cleavable in the vicinity of the target site. Cleavage of the linker to release the fusion partner from the antibody may be prompted by enzymatic activity or conditions to which the immunoconjugate is subjected in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to fXI is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody that specifically binds fXI can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect fXI by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

VIII. Pharmaceutical Compositions and Methods of Administration

The anti-fXI monoclonal antibodies (and antigen-binding fragments thereof) of the disclosure can be formulated according to known methods for preparing pharmaceutically useful compositions, such as by admixture with a pharmaceutically acceptable carrier vehicle. Suitable vehicles and their formulations are described, for example, in Remington's Pharmaceutical Sciences (16th ed., Osol, A. (ed.), Mack, Easton Pa., 1980). In order to form a pharmaceutically acceptable composition suitable for effective administration, such compositions will contain an effective amount of the anti-fXI monoclonal antibody either alone, or with a suitable amount of carrier vehicle.

Pharmaceutical compositions can be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Furthermore, pharmaceutical compositions can be formulated for immediate release or controlled release.

Pharmaceutical compositions comprising one or more anti-fXI monoclonal antibodies of the disclosure can be administered in dosages and by techniques well known to those skilled in the medical or veterinary arts, taking into consideration such factors as the age, sex, weight, species and condition of the particular subject, and the route of administration. The amount and timing of administration are at the discretion of the treating physician or veterinarian to achieve the desired purposes. The route of administration can be via any route that delivers a safe and therapeutically effective dose (or inhibitory dose) of an anti-fXI monoclonal antibody disclosed herein to the blood of an animal or human. The antibody can be formulated for systemic or local administration. Forms of administration, include, but are not limited to, systemic, topical, enteral, and parenteral routes of administration. Enteral routes include oral and gastrointestinal administration. Parenteral routes include intravenous, intraarterial, intramuscular, intraperitoneal, subcutaneous, transdermal, and transmucosal administration. Other routes of administration include epidural or intrathecal administration. In one example, the antibody that specifically binds fXI is formulated for parenteral administration, such as intravenous administration.

The effective dosage and route of administration are determined by the therapeutic range and nature of the compound, and by known factors, such as the age, weight, and condition of the subject, as well as LD$_{50}$ and other screening procedures that are known and do not require undue experimentation. The therapeutic agent can be delivered to the recipient as a bolus or by a sustained (continuous or intermittent) delivery. When the delivery of a dosage is sustained over a period, which may be in the order of a few minutes to several days, weeks or months, or may be administer chronically for a period of years, the dosage can be expressed as weight of the therapeutic agent/kg body weight of the patient/unit time of delivery.

By "therapeutically effective dose or amount" or "effective amount" is intended an amount of an anti-fXI monoclonal antibody or functional fragment thereof that when administered brings about a positive therapeutic response with respect to treatment of a patient in need thereof. Generally, a therapeutically effective dose is similar to the "inhibitory dose" or "inhibitory amount" which terms refer to the dose of fXI-specific antibody required to inhibit activation of fXI. In some embodiments, a therapeutically effective amount of the anti-fXI monoclonal antibody is in the range from about 0.01 mg/kg to about 10 mg/kg, from about 0.1 mg/kg to about 10 mg/kg, from about 1 mg/kg to about 10 mg/kg, from about 1 mg/kg to about 5 mg/kg, from about 0.01 mg/kg to about 1 mg/kg, or from about 0.1 mg/kg to about 1 mg/kg. In other embodiments, the therapeutically effective doses of anti-factor XI monoclonal antibody, is about 0.01 mg/kg, about 0.03 mg/kg, about 0.1 mg/kg, about 0.3 mg/kg, about 0.5 mg/kg, about 1 mg/kg, about 1.5 mg/kg, about 2 mg/kg, about 2.5 mg/kg, about 3 mg/kg, about 5 mg/kg, about 7 mg/kg, about 10 mg/kg, or other such doses falling within the range of about 0.01 mg/kg to about 10 mg/kg. It is recognized that the method of treatment may comprise a single administration of a therapeutically effective dose (or inhibitory dose) or multiple administrations of a therapeutically effective dose of the anti-fXI monoclonal antibody.

In some embodiments, the inhibitory dose (or therapeutically effective dose) of an antibody (whether alone or as part of an immunoconjugate or composition of the present disclosure) is a dose that inhibits fXI activation by at least 50%, at least 60%, at least 70%, at least 80%, at least 90%, at least 95%, at least 99% or 100%. In particular examples, fXI activation is inhibited 90-100%.

In some embodiments, the antibodies are administered daily, every other day, bi-weekly or weekly. In specific examples, the antibodies are administered daily or bi-weekly. In the methods disclosed herein, administration of an "antibody" includes antibodies that are part of immunoconjugates of compositions of the disclosure.

Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Compositions are provided that include one or more of the antibodies that specifically bind fXI that are disclosed herein in a carrier. Compositions comprising immunoconjugates are also provided. The compositions can be prepared in unit dosage forms for administration to a subject.

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs.

Controlled release (or extended release) parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303 ; 5,514,670; 5,413,797; 5,268,164; 5,004,697; 4,902,505 ; 5,506,206; 5,271,961; 5,254,342 and U.S. Pat. No. 5,534,496).

IX. Methods of Use of Anti-Factor XI Antibodies

The antibodies specific for fXI disclosed herein can be used for a variety of research, diagnostic and therapeutic purposes. For example, the disclosed antibodies can be used to study the effects of blockade of fXI activation and/or inhibition of fXI binding to fXIIa. fXI-specific antibodies can also be used to purify fXI from mammals or from recombinant cell products. In addition, the disclosed antibodies are useful as diagnostic reagents, such as for the detection of fXI in a blood, tissue or other biological sample.

Accordingly, provided herein is a method of purifying fXI from a biological sample by contacting the sample with a monoclonal antibody, or antigen-binding fragment thereof, disclosed herein is also provided. For example, the fXI-specific antibodies of the disclosure can be used to immunoprecipitate fXI from any biological sample of any mammalian species. Methods of immunoprecipitation are well known in the art. In some examples, the fXI-specific antibody is conjugated to a bead, such as a magnetic bead that allows for efficient separation of antibody bound to antigen (e.g., fXI bound to a fXI-specific antibody). The biological sample can be any sample where fXI protein is found. In some examples, the biological sample is a fluid sample, such as a blood, serum or plasma sample, or a tissue sample.

Further provided is a diagnostic method of detecting fXI in a biological sample, or measuring the level of fXI in a biological sample. In some examples, the biological sample is a fluid sample, such as a blood, serum or plasma sample, or a tissue sample. Methods of detecting proteins in a biological sample, or measuring the level of a protein in a biological sample, are well known in the art.

Moreover, because of the significant role that coagulation pathways (or the disruption thereof) play in numerous diseases and disorders, the anti-fXI antibodies disclosed herein can be used for a wide range of therapeutic purposes. The fXI-specific antibodies disclosed herein can be used to prevent, treat or ameliorate any disease or disorder in which inhibition of fXI activation would result in prevention or treatment of the disease or disorder. The disclosed fXI antibodies are desirable as therapeutic agents because of their ability to prevent or inhibit thrombosis without altering hemostasis.

In some embodiments, the disclosed fXI-specific antibodies can be used for the prevention or treatment of a disease or disorder characterized by the pathological activation of fXI. For example, such diseases or disorders include those where inhibition of the contact activation of coagulation would benefit the subject having the disease or disorder.

In some embodiments, the disclosed anti-fXI antibodies can be used to prevent or treat thrombosis or thromboembolism in a subject in need of such treatment. As disclosed herein, administration of the anti-fXI antibodies does not alter hemostasis in the subject.

In one embodiment, the anti-fXI monoclonal antibodies of the disclosure can be used to treat conditions characterized by vascular occlusions, such as those that occur as a result of thrombus formation. Conditions that are characterized by vascular occlusions that are contemplated for treatment with an anti-fXI monoclonal antibody include those that involve the arterial, capillary, and venous vasculature. In the coronary arteries, occlusive thrombus formation often follows the rupture of atherosclerotic plaque. This occlusion is the major cause of acute myocardial infarction and unstable angina. Coronary occlusions can also occur following infections, inflammation, thrombolytic therapy, angioplasty, and graft placements. Similar principles apply to other parts of the arterial vasculature and include, among others, thrombus formation in the carotid arteries, which is the major cause of transient or permanent cerebral ischemia and stroke.

In particular examples, the described antibody molecules are used to treat vascular diseases, such as ischemic or nonischemic heart disease, or stroke. In other examples, the fXI-specific antibodies are used to treat atherosclerotic diseases.

Venous thrombosis often follows stasis, infections, inflammatory reactions, and major surgery of the lower extremities or the abdominal area. Deep vein thrombosis results in reduced blood flow from the area distal to the thrombus and predisposes to pulmonary embolism. Pulmonary embolism is a major cause of post-surgical mortality. Disseminated intravascular coagulation (DIC) and acute respiratory distress syndrome (ARDS) commonly occur within all vascular systems during bacterial sepsis, entry of foreign material into the bloodstream following, for example, trauma and child birth, immune reactions, inflammation, certain viral infections, certain platelet disorders, and cancer. Disseminated intravascular coagulation is a severe complication of many disease conditions and some drug treatments, including, for example, heparin. Thrombotic consumption of coagulation factors and platelets, and systemic coagulation, results in the formation of life-threatening thrombi occurring throughout the microvasculature—leading to local or widespread hypoxia and organ failure.

Thus, in one embodiment, a method is provided for inhibiting thrombosis in a subject in need thereof by administering to the subject a therapeutically effective dose (or an inhibitory dose) of an anti-factor XI monoclonal antibody of the disclosure. In some examples, the thrombosis is associated with (i) acute coronary syndromes, such as myocardial infarction, unstable angina, refractory angina, occlusive coronary thrombus occurring post-thrombolytic therapy or post-coronary angioplasty; (ii) ischemic cerebrovascular syndromes, including embolic stroke, thrombotic stroke, or transient ischemic attacks; (iii) thrombosis occurring in the venous system occurring either spontaneously or in the setting of malignancy, trauma, or surgery, including pulmonary thromboembolism; (iv) any coagulopathy including ARDS and DIC, for example in the setting of sepsis or other infection, surgery, pregnancy, trauma, or malignancy and whether associated with multi-organ failure or not, thrombotic thrombocytopenic purpura, thromboangiitis obliterans, or thrombotic disease associated with heparin-induced thrombocytopenia; (v) thrombotic complications associated with extracorporeal circulation (for example, renal dialysis, cardiopulmonary bypass or other oxygenation procedure, and plasmapheresis); (vi) thrombotic complications associated with instrumentation (such as cardiac or other intravascular catheterization, intraaortic balloon pump, coronary stent, cardiac valve, dialysis machines, pumps and oxygenators); (vii) complications associated with fitting of prosthetic devices; and (ix) foreign thrombogenic material in the circulation (natural or artificial), such as from surgical procedures, organ/tissue/cell transplantation (e.g., graft versus host reaction), or implants.

Traditional antithrombotic agents can have negative side effects, and even be fatal, when administered at their maximally effective doses. Accordingly, in another embodiment, a method is provided for reducing a required dose or complementing the effect of an antithrombotic agent in the treatment of thrombosis in a subject in need thereof by administering to the subject a therapeutically effective dose of an anti-fXI monoclonal antibody of the disclosure.

Antithrombotic agents include, for example, direct or indirect thrombin inhibitors, factor X (fX) inhibitors, factor IX (fIX) inhibitors, factor XII (fXII) inhibitors, factor V (fV) inhibitors, factor VIII (fVIII) inhibitors, factor XIII (fXIII) inhibitors, factor VII (fVII) inhibitors, tissue factor inhibitors, profibrinolytic agents, fibrinolytic agents, carboxypeptidase B inhibitors, platelet inhibitors, selective platelet count reducing agents, or fXI inhibitors. Direct thrombin inhibitors include argatroban and derivatives or analogs thereof, hirudin and recombinant or synthetic derivatives or analogs thereof, derivatives of the tripeptide Phe-Pro-Arg, chloromethylketone derivatives, ximelagatran and derivatives, metabolites, or analogs thereof, anion binding exosite inhibitors, and RNA/DNA aptamers. Indirect thrombin inhibitors include heparin, coumarin, dermatan, and thrombomodulin. fX inhibitors include direct fXa inhibitors, rivaroxaban, antibodies to fX, inactivated fXa, or analogs and derivatives thereof.

fIX inhibitors include antibodies to fIX, direct fIXa inhibitors, or inactivated fIXa, or analogs and derivatives thereof. fXII inhibitors include direct fXII inhibitors, corn trypsin inhibitor, antibodies to fXII, or inactivated fXIIa or analogs and derivatives thereof. Factor V inhibitors include antibodies to fV, activated protein C, protein S, or analogs and derivatives thereof. Factor VIII inhibitors include antibodies to fVIII, activated protein C, protein S, or analogs and derivatives thereof. Factor XIII inhibitors include antibodies to fXIII, direct fXIIIa inhibitors, or inactivated fXIIIa. Factor VII inhibitors include antibodies to fVII, tissue factor pathway inhibitor, inactivated fVIIa, or direct factor VIIa inhibitor or analogs and derivatives thereof. Tissue factor inhibitors include tissue factor pathway inhibitor, antibodies to tissue factor, or analogs and derivatives thereof. Profibrinolytic agents include urokinase, streptokinase, tissue plasminogen activator or derivatives thereof.

Fibrinolytic agents include plasmin, microplasmin, ancrod, or derivatives thereof. Platelet inhibitors include aspirin, clopidogrel, dypiridamol, or derivatives thereof. Selective platelet count reducing agents include hydroxyurea, anagrelide, or derivatives thereof. Factor XI inhibitors include direct fXIa inhibitors, other antibodies to fXI, inactivated fXIa, or analogs and derivatives thereof.

In another embodiment, a method is provided for treating metastatic cancer in a subject in need thereof by administering to the subject a pharmaceutically effective dose (or inhibitory dose) of an anti-fXI monoclonal antibody of the disclosure. In yet another embodiment, a method is provided for treating an acute inflammatory reaction in a subject in need thereof by administering to the subject a therapeutically effective dose (or an inhibitory dose) of an anti-fXI monoclonal antibody of the disclosure. In another embodiment, the fXI antibodies disclosed herein can be used to treat amniotic fluid or bone marrow embolism. In another embodiment, the disclosed antibodies can be used treat sickle cells disease or hemolysis. Further provided is a method of treating acute Glomerulonephritis in subject in need of treatment by administering to the subject a fXI-specific antibody of the disclosure. A method of treating diabetic retinopathy in a subject in need of treatment by administering to the subject an anti-fXI antibody discloses herein is also provided.

In further embodiments of the present disclosure, combination therapies are provided in which an anti-fXI monoclonal antibody is the primary active agent and is administered along with an additional active agent to a subject in need thereof. Such combination therapy can be carried out by administration of the different active agents in a single composition, by concurrent administration of the different active agents in different compositions, or by sequential administration of the different active agents. The combination therapy can also include situations where the anti-fXI monoclonal antibody is already being administered to the patient, and the additional active agent is to be added to the patient's drug regimen, as well as where different individuals (for example, physicians or other medical professionals) are administering the separate components of the combination to the patient. The additional active agent will generally, although not necessarily, be one that is effective in inhibiting thrombosis. In some embodiments, the additional active agent is a hemostatic agent (i.e., an agent that promotes hemostasis). In particular examples, the hemostatic agents used in combination therapies include activated factor VII (fVIIa) or activated prothrombin complex concentrate (APCC). The key active ingredient of APCC is prothrombin, which contributes to both hemostasis and thrombus growth. By contrast, increasing the plasma concentration of FVIIa is thought to increase the generation of thrombin predominantly through a tissue factor (TF)-dependent pathway in which the TF/fVIIa complex activates factors IX and X.

In particular embodiments, the method of inhibiting activation of fXI by factor XIIa (fXIIa) in a subject comprises (a) selecting a subject in need of treatment; and (b) administering to the subject an inhibitory amount of a monoclonal antibody, immunoconjugate or the composition disclosed herein. In some examples, the subject in need of treatment has or is at risk of developing thrombosis. In some examples, the subject in need of treatment is a subject suffering from or at risk of suffering from myocardial infarction, ischemic stroke, pulmonary thrombo-embolism, disseminated intravascular coagulation, severe systemic inflammatory response syndrome, metastatic cancer, or an infectious disease. In some examples, the subject in need of treatment is a subject with pathological activation of fXI. In some examples, the inhibitory amount of the monoclonal antibody, immunoconjugate or composition is an amount sufficient to inhibit activation of fXI by at least 50%, at least 60%, at least 70%, at least 80%, at least 90%, at least 95%, at least 99% or 100%. In particular examples, the inhibitory amount of the monoclonal antibody, immunoconjugate or composition is an amount sufficient to inhibit activation of fXI by 90-100%. The antibody, immunoconjugate or composition can be administered using any suitable route of administration, and any suitable dose or dosing schedule, as discussed above.

The following examples are provided to illustrate certain particular features and/or embodiments. These examples should not be construed to limit the disclosure to the particular features or embodiments described.

EXAMPLES

Example 1

Generation, Sequencing and Characterization of fXI-Specific Monoclonal Antibody 14E11

Figure 8:
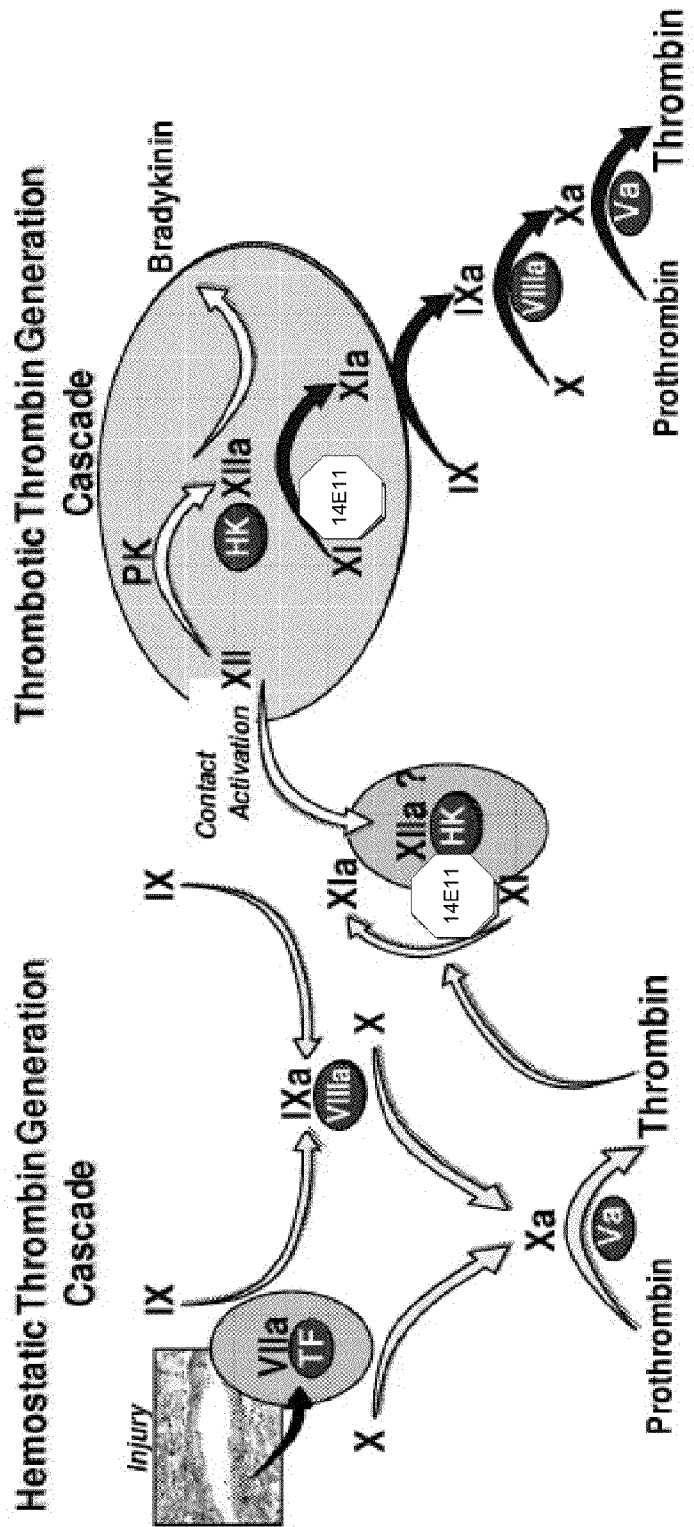
FIG. 8 is a schematic depicting the hemostatic and thrombotic thrombin generation cascades. Monoclonal antibody 14E11 blocks activation of fXI by fXIIa.

This example describes the production and sequencing of a monoclonal antibody specific for fXI that blocks interaction of fXI with fXIIa (see FIG. 8).

Generation and Sequencing of 14E11

Monoclonal IgG 14E11 was raised against murine fXI in a fXI-deficient mouse. To determine the amino acid and nucleotide sequences of the variable light chain and variable heavy chain of 14E11, $V_L$-$C_L$ and $V_H$-$C_{H1}$ were cloned from the 14E11 hybridoma according to standard procedures. The variable light chain and heavy chain amino acid and nucleotide sequences were determined and are set forth below and in the sequence listing as SEQ ID NOs: 1-4. The CDR residues are underlined and are listed in Table 1 below.

```
Amino acid sequence of the
14E11 variable light (V_L) chain
                                      (SEQ ID NO: 1)
DIVMTQSHKFMSTSVGDRVSITCKASQDVSTAVAWYQQKPGQSPKLLIYL
TSYRNTGVPDRFTGSGSGTDFTFTISSVQAEDLAVYYCQQHYKTPYSFGG
GTKLERLR Nucleotide sequence of the
14E11 variable light (V_L) chain
                                      (SEQ ID NO: 2)
GACATTGTGATGACCCAGTCTCACAAATTCATGTCCACATCAGTAGGAGA
CAGGGTCAGCATCACCTGCAAGGCCAGTCAGGATGTGAGTACTGCTGTTG
CCTGGTATCAACAGAAACCAGGACAATCTCCTAAACTACTGATTTACTTG
ACATCCTACCGGAACACTGGAGTCCCTGATCGCTTCACTGGCAGTGGATC
TGGGACGGATTTCACTTTCACCATCAGCAGTGTGCAGGCTGAAGACCTGG
CAGTTTACTACTGTCAGCAACATTATAAAACTCCGTATTCGTTCGGAGGG
GGGACCAAGCTGGAACGGTTACGG
```

-continued

Amino acid sequence of the
14E11 variable heavy (V$_H$) chain
(SEQ ID NO: 3)
QVQLEESGPGLVAPSQSLSITCTVSGFSLT<u>GYGIY</u>WVRQPPGKGLEWLG<u>M
IWGDGRTDYNSALKSRLSI</u>SKDNSKSQVFLKMNSLQTDDTARYYCAR<u>DYY
GSKDY</u>WGQGTTLTVSS Nucleotide sequence of the
14E11 variable heavy (V$_H$) chain
(SEQ ID NO: 4)
CAGGTGCAGCTGGAGGAGTCAGGACCTGGCCTGGTGGCGCCCTCACAGAG
CCTGTCCATCACATGCACCGTCTCAGGGTTCTCATTAACCGGCTATGGTA
TATACTGGGTTCGCCAGCCTCCAGGAAAGGGTCTGGAGTGGCTGGGAATG
ATATGGGGTGATGGAAGAACAGACTATAATTCAGCTCTCAAATCCAGACT
GAGCATCAGTAAGGACAACTCCAAGAGCCAAGTTTTCTTAAAAATGAACA
GTCTGCAAACTGATGACACAGCCAGGTACTACTGTGCCAGAGATTACTAC
GGTAGTAAGGACTACTGGGGCCAAGGCACCACTCTCACAGTCTCCTCA

TABLE 1

Locations of the CDRs in 14E11 V$_L$ and V$_H$

| Chain | CDR | Residues | SEQ ID NO: |
|---|---|---|---|
| V$_L$ | CDR1 | 24-34 | 1 |
| V$_L$ | CDR2 | 50-63 | 1 |
| V$_L$ | CDR3 | 91-98 | 1 |
| V$_H$ | CDR1 | 31-35 | 3 |
| V$_H$ | CDR2 | 50-68 | 3 |
| V$_H$ | CDR3 | 98-105 | 3 |

14E11 Universally Recognizes Mammalian fXI

The capacity of 14E11 to bind fXI from different mammalian species was evaluated by immunoprecipitation. Plasma was obtained from human, cattle, horse, pig, rabbit, raccoon, tiger, baboon, cat, chicken, dog African elephant and llama subjects, and serum was obtained from anteater. Plasma from a fXI-deficient human subject was used as a negative control. Plasma or serum (500 µl) was collected into sodium citrate and mixed with 500 µl Tris-HCl. 14E11 antibody was linked to Affigel-10 at 3 mg IgG per ml of beads. The diluted plasma or serum (1 ml) was immunoprecipitated with 50 µl of 14E11 beads overnight at 4° C. The beads were washed once with 1 ml Tris-HCl, then eluted with 50 µl of non-reducing SDS-sample buffer. Eluate (1-10 µl) was run on 7.5% SDS gels under non-reducing conditions. Western blots of the gels were performed using biotinylated 14E11 as the primary antibody and streptavidin-HRP as the secondary antibody.

Figure 9:
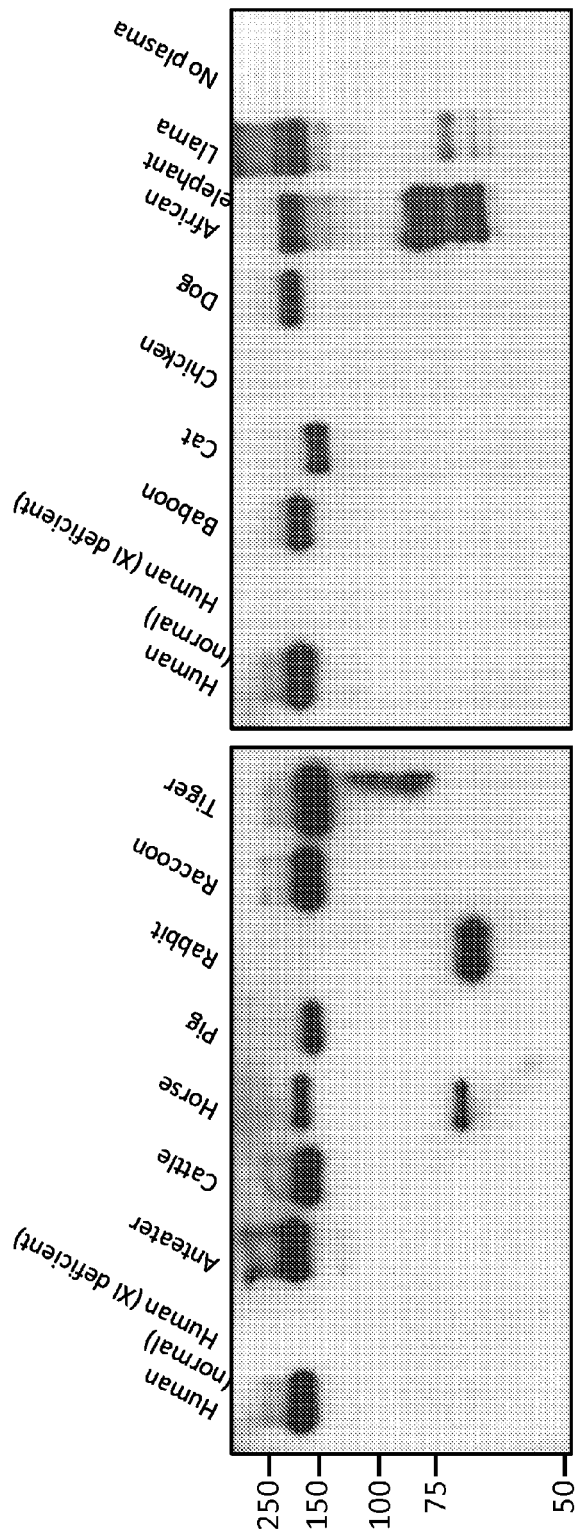
FIG. 9 shows an immunoblot of fXI immunoprecipitated from plasma collected from a variety of mammalian species and one avian species (chicken). Plasma or serum was obtained from the indicated species and immunoprecipitated with 14E11. The eluate was separated on polyacrylamide-SDS gels and immunoblotted with biotinylated 14E11, followed by streptavidin-HRP.

The results demonstrate the 14E11 recognizes fXI from a variety of mammalian species, including humans, anteaters, cows, horses, pigs, rabbits, raccoons, tigers, baboons, cats, dogs, elephants and llamas (FIG. 9). As expected, 14E11 did not recognize any proteins in the sample obtained from a chicken because avian species do not express fXI.

14E11 Binds the A2 Domain of fXI

Figure 10B:
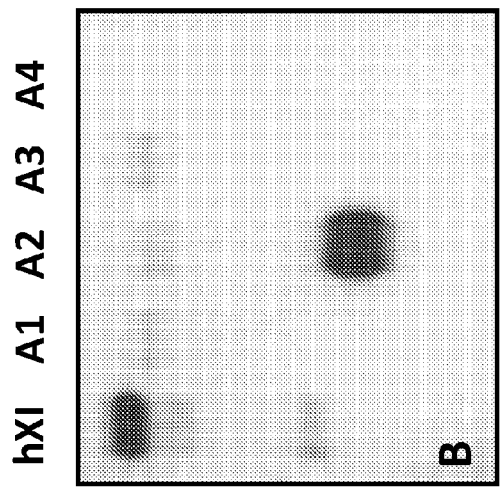
FIGS. 10A and 10B are immunoblots of recombinant fXI proteins. (A) Chimeric proteins were generated in which the four individual fXI apples domains (A1-A4) were swapped with the corresponding domain from prekallikrein (PK). The chimeric proteins were separated by electrophoreses and immunoblotted with 14E11. (B) Fusion proteins were generated in which each individual apple domain from fXI was fused to tissue plasminogen activator (tPA). The fusion proteins were separated by electrophoresis and immunoblotted with 14E11.
Figure 10A:
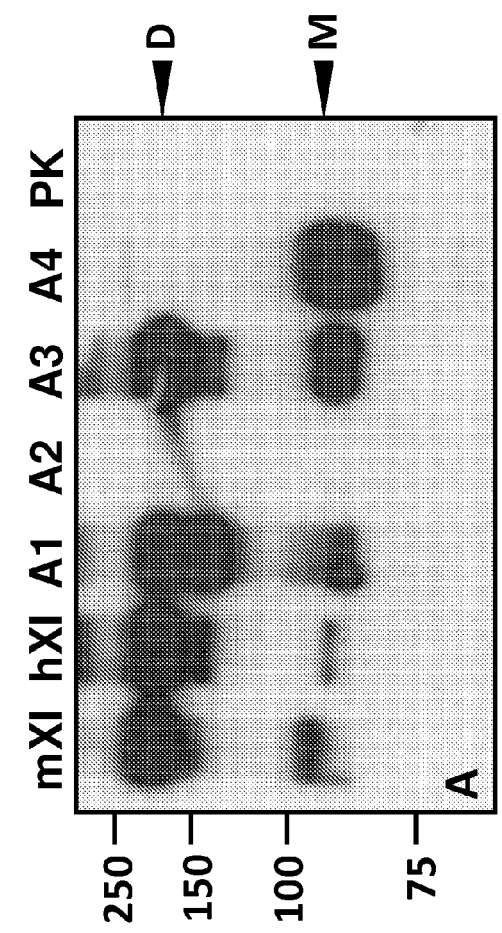

In order to determine which domain of fXI 14E11 binds, a series of chimeric constructs were generated in which the four individual fXI apples domains (A1-A4) were swapped with the corresponding domain from PK. The chimeric proteins were separated by electrophoreses and immunoblotted with 14E11. The results demonstrated that 14E11 recognized murine and human wild-type fXI, as well as chimeric proteins comprising the fXI A1, A3 or A4 domain (see FIG. 10A). However, 14E11 did not recognize the chimeric protein lacking the A2 domain of fXI. These results indicate that 14E11 binds an epitope present in the A2 domain. Individual fXI apple domains also were fused to tPA to determine whether 14E11 is capable of binding to specific domain. The fusion proteins were separated by electrophoreses and immunoblotted with 14E11. The results demonstrate that 14E11 binds the A2 domain, but does not bind the A1, A3 or A4 domains of fXI (FIG. 10B).

Animals treated with 14E11 are protected from carotid artery occlusion

Monoclonal antibody 14E11 was evaluated in a murine carotid artery thrombosis model. C57B1/6 mice were treated with 7.5% or 10% FeCl$_3$ and administered 14E11 either intravenously or intraperitoneally. In the absence of 14E11 treatment, all animals developed occlusions following treatment with either concentration of FeCl$_3$ within 10 minutes. However, none of the mice (10 of 10) treated with 7.5% FeCl$_3$ and 14E11 developed occlusion of the carotid artery. Immunoblots for fXI demonstrated that treatment with 14E11 did not reduce the amount of fXI present in the plasma of treated animals. This finding is consistent with the data presented below, which indicates that the anti-thrombic effect of 14E11 results from preventing activation of fXI by fXIIa.

Example 2

Inhibition of Thrombus Formation in a Baboon Model of Thrombosis

The baboon thrombosis model has been previously described by Tucker et al. (*Blood* 113(4):936-944, 2009) and in PCT Publication NO. WO 2009/067660. Experiments to evaluate collagen-induced thrombus formation in the presence or absence of 14E11 were carried out as described below.

Thrombus formation was initiated within chronic arteriovenous shunts in baboons by interposing a prosthetic vascular graft for up to 60 minutes according to a previously described procedure (Hanson et al., *J. Clin. Invest.* 92:2003-2012, 1993). The hypothrombogenic graft (expanded-polytetrafluoroethylene; W.L. Gore & Associates, Flagstaff, Ariz.; Gruber and Hanson, *Blood* 102:953-955, 2003) was coated with collagen, which consistently triggers platelet-dependent thrombus formation. Graft segments 20 mm in length (with internal diameters of either 2 or 4 mm) were filled with equine type I collagen (1 mg/ml; Nycomed Arzeneimittel, Munich, German) for 15 minutes, and then dried overnight under sterile airflow. The thrombogenic collagen-coated grafts were then incorporated between segments of silicon rubber tubing, deployed into the shunts, and exposed to blood flow. The flow rate through the graft was restricted to 100 ml/minute (measured by the Transonics Systems flow meter, Ithaca, N.Y.) by clamping the proximal shunt segment, thereby producing initial mean wall-shear rates of 265 s$^{-1}$ (4 mm internal diameter) or 2120 s$^{-1}$ (2 mm internal diameter). The grafts were removed from the shunts either at 60 minutes (4 mm internal diameter grafts) or when the flow rate fell from 100 ml/minute to 20 ml/minute (2 mm internal diameter grafts), signaling imminent occlusion. The time from initiation of blood flow through the graft until the flow reached 20 ml/minute was taken as the occlusion time.

Thrombus formation was assessed in real time during the experiments by quantitative gamma camera imaging of radiolabeled platelet accumulation within the raft segment, and by end-point determinations of radiolabeled fibrinogen/fibrin deposition, as described previously (Hanson et al., *J. Clin. Invest.* 92:2003-2012, 1993). Measurements of platelet-associated radioactivity on the grafts were recorded using a General Electric (Milwaukee, Wis.) 400T gamma scintillation camera interfaced with a NuQuest InteCam computer system (MECX, Arlington Heights, Ill.). Embolic event were recorded as abrupt decreases in the number of platelets in the graft between subsequent imaging frames.

Animals were either treated with vehicle, aspirin, monoclonal antibody O1A6 (described in Tucker et al., *Blood* 113(4):936-944, 2009; and in PCT Publication NO. WO 2009/067660), or monoclonal antibody 14E11. In accordance with previous results, treatment with O1A6 reduced platelet and fibrin deposition in 4 mm internal diameter collagen-coated vascular grafts. In contrast, treatment with 14E11 did not significantly alter platelet or fibrin deposition in collagen-coated grafts. However, administration of 14E11 did significantly reduce platelet deposition in a propagating tail thrombus.

Blocking the propagating tail thrombus without significantly effecting platelet deposition in the thrombogenic trigger graft is a result that characterizes effective antithrombotic agents, such as high dose heparin. Thus, the results disclosed herein indicate that that 14E11 is a potent antithrombotic agent in primates.

Example 3

Materials and Methods

This example describes the reagents, assays and methods used in the studies described in Example 4.

Reagents fXII-deficient plasma was from George King Bio-Medical, Inc. fXI, fXIa, factor Xa (fXa), α-thrombin, and fXI-deficient plasma were from Hematologic Technologies. Recombiplastin tissue factor was from Instrument Laboratories. fXIIa and corn-trypsin-inhibitor (CTI) were from Enzyme Research Laboratories. Recombinant hirudin (Lepirudin) was from Bayer. S-2366 (L-pyro-glutamyl-L-prolyl-L-arginine-p-nitroanilide) was from DiaPharma. Z-Gly-Gly-Arg-AMC was from Bachem. Dioleoylphosphatidylcholine:dioleoylphosphatidylserine (7:3 wt/wt) was from Avanti Polar Lipids. STA PTT Automate 5 reagent was from Diagnostic Stago. Bovine serum albumin (BSA), rabbit brain cephalin (RBC) and diisopropylfluorophosphate (DFP) were from Sigma-Aldrich. Thrombin-α2-macroglobulin calibrators for thrombin generation assays were from Thrombinoscope (Maastricht, The Netherlands).

Expression and Purification of Recombinant Factor XI

Recombinant human fXI was expressed in HEK 293 cells, as previously described (Sun et al., *J. Biol. Chem.* 274:36373-36378, 1999). cDNAs expressed were for (1) wild type fXI ($fXI^{WT}$), (2) fXI with $Lys^{83}$ and $Gln^{84}$ replaced with alanine ($fXI-Ala^{83-84}$), (3) fXI with $Ser^{195}$, $Asn^{196}$, and $Ile^{197}$ replaced with alanine ($fXI-Ala^{195-197}$), and (4) fXI with $Ser^{557}$ replaced with alanine ($fXI-Ala^{557}$). fXI was purified from conditioned media (Cellgro Complete) by chromatography using anti-human factor XI-IgG 1G5.12 (Sun et al., *J. Biol. Chem.* 274:36373-36378, 1999). Protein was eluted with 2 M sodium thiocyanate in 50 mM Tris-HCl pH 7.5, 100 mM NaCl (Tris/NaCl), concentrated by ultrafiltration, dialyzed against Tris/NaCl, and stored at −80° C. fXI (approximately 200 μg/ml) was converted to fXIa by incubation with 2 μg/ml fXIIa at 37° C. fXIa was separated from fXIIa by reapplying it to the 1G5.12 affinity column.

Characterization of recombinant factor XI fXI $fXI^{WT}$ and fXI variants were diluted to 5 μg/ml in 50 mM Tris-HCl pH 7.4, 100 mM NaCl, 0.1% BSA (TBSA), and serial 1:2 dilutions of each protein were prepared. Each dilution (65 μl) was mixed with equal volumes of fXI-deficient plasma and STA PTT Automate 5 reagent (Diagnostic Stago) and incubated for five minutes at 37° C. After incubation, 65 μl of 25 mM $CaCl_2$ was added, and time to clot formation was determined on a Dataclot II fibrometer (Helena Laboratories). Results for 5 μg/ml $fXI^{WT}$ were designated 100% activity. The specific activity of $fXI^{WT}$ was similar to plasma fXI (approximately 200 units/mg, with 1 unit representing the fXI activity in 1 ml of normal plasma). Results for dilutions of fXI were plotted against clotting time, and specific activities determined relative to $fXI^{WT}$. Activities of fXIa in plasma were compared by adding 65 μl of serial dilutions of protease to equal volumes of fXI-deficient plasma and RBC. After 30 seconds, 65 μl of 25 mM $CaCl_2$ was added and time to clot formation was determined. The activities of fXIa were determined relative to 5 μg/ml $fXIa^{WT}$ (assigned a value of 100%).

$fXI^{WT}$ and $fXI-Ala^{83-84}$ were diluted to 25 nM in TBSA with 5 nM fXIIa or 15 nM α-thrombin at 37° C. At 10 minute intervals, 50 μl aliquots were removed and supplemented with 750 μM CTI (for fXIIa) or 150 μM lepirudin (for α-thrombin) to terminate activation. Samples were mixed with equal volumes of TBSA containing 1 mM S-2366 and changes in OD 405 nm were followed on a SpectraMAX microtiter plate reader (Molecular Devices). fXIa concentration was determined by comparison to a standard curve constructed with pure fXIa. In some reactions, monoclonal antibodies to fXI were included.

Characterization of murine anti-fxi monoclonal antibodies O1A6 and 14E11

Murine monoclonal IgG O1A6 was raised against human fXI (Tucker et al., *Blood* 113(4):936-944, 2009). The antibody prolongs the clotting time of human plasma ($IC_{99}$ of approximately 10 nM) in a partial thromboplastin time (PTT) assay). Monoclonal IgG 14E11 was raised in a fXI-deficient Balb-C mouse against recombinant murine fXI (Gailani et al., *Blood* 90:1055-1064, 1997). This antibody prolongs the PTT of mouse and human plasma. Preparation of recombinant human fXI, prekallikrein (PK), and fXI/PK chimeras has been described (Sun and Gailani, *J. Biol. Chem.* 271:29023-29028, 1996). Western blots of recombinant proteins size-fractionated on 10% polyacrylamide-SDS gels were performed using O1A6 or 14E11 as the primary detection antibody and chemiluminescence for detection. The effect of O1A6 and 14E11 on fXI activation was tested using the chromogenic assay described above.

Isolation of Platelets from Human Blood

Blood was drawn from healthy volunteers into a one-tenth volume of acid citrate dextrose anticoagulant, followed by sedimentation at 200 g for 20 minutes at room temperature. Platelet rich plasma (PRP) was removed from the pellet. Platelets were pelleted in the presence of 1 U/ml VII grade Apyrase (Sigma) at 800 g for 20 minutes, resuspended in Tyrode buffer (15 mM Hepes pH 6.5, 125 mM NaCl, 2.7 mM KCl, 1 mM $MgCl_2$, 0.4 mM $NaH_2PO_4$, 5.6 mM dextrose, 0.35% BSA), and passed over a Sepharose 4B (Sigma) size exclusion column (Baglia et al., *J. Biol. Chem.* 270:6734-6740, 1995). After pelleting at 800 g for 20 minutes, platelets were resuspended in Tyrode buffer pH 7.4, and counted on a Hemavet HV950FS multispecies hematology instrument (Drew Scientific).

Thrombin generation assay

Thrombin generation was determined by measuring cleavage of the fluorogenic substrate Z-Gly-Gly-Arg-AMC at 37° C. on a Thrombinoscope® (Mastricht, The Netherlands), using the internal α-thrombin/a2-macroglobulin calibrators supplied by the manufacturer (Hemker et al., *Thromb. Haemost.* 83:589-591, 2000; De Smedt et al., *Thromb. Haemost.* 100:343-349, 2008). Thrombin generation studies were performed in 96-well plates (Immulon 2HB, Thermo Scientific, Waltham, Mass.). Prior to use, wells were coated by adding 200 µl of 10 mg/ml PEG 20000 followed by incubation overnight at room temperature. After removal of blocking solution, plates were heated in an oven overnight at 65° C. Prior to use in CAT assays, all preparations of plasma and recombinant fXI (0.7-1.9 µM in Tris/NaCl) were treated with a 1000-fold molar excess of DFP for 30 minutes, at room temperature, followed by dialysis against Tris/NaCl.

Using plasmas from different donors and different phlebotomies from the same donor can introduce significant variation into thrombin generation assays. Therefore, experiments were performed using single lots of fXI- or fXII-deficient plasma. Plasmas were supplemented with 50 µg/ml CTI and 415 µM Z-Gly-Gly-Arg-AMC HCl, final concentrations. fXI-deficient plasma was supplemented with fXI (30 nM) or vehicle. fXII-deficient plasma was supplemented with O1A6 or 14E11 IgG (300 nM) or vehicle and incubated for 30 minutes on ice prior to use. Addition of supplements resulted in <10% dilution of the original plasma.

In each microtiter plate well, 80 µl supplemented plasma was mixed with 20 µl Tyrode buffer pH 7.4 containing phosphatidylcholine/phosphatidylserine vesicles (30 µM) or gel-filtered platelets (600,000/mm$^3$) and either tissue factor (0.96-9.6 pM), α-thrombin (30-300 nM), fXa (36-180 pM) or fXIIa (0.6-6 nM). Final concentrations are 5 µM phosphatidylcholine/phosphatidylserine vesicles, 100,000/mm$^3$ platelets, 0.16-1.6 µM TF, 5-50 nM α-thrombin, 6-30 µM fXa, or 0.1-1 nM fXIIa. For controls, 80 supplemented plasma was mixed with 20 µl calibrator. Reactions were initiated by adding 20 µl of 20 mM HEPES pH 7.4, 100 mM CaCl$_2$, 6% BSA, using the injection system of the Thrombinoscope, and fluorescence was monitored (excitation λ 390 nM, emission λ 460 nM). Thrombin generation was determined using Thrombinoscope® Analysis software, version 3.0. The area under the thrombin generation curves is referred to as the endogenous thrombin potential (ETP).

Example 4

Factor XI Contributes to Thrombin Generation in the Absence of Factor XII fXI-Dependent Thrombin Generation in fXI-Deficient Plasma Supplemented with Plasma fXI.

The contribution of fXI to coagulation was assessed by measuring thrombin-mediated cleavage of a fluorogenic substrate, as described previously (Hemker et al., Thromb. Haemost. 83:589-591, 2000; De Smedt et al., Thromb. Haemost. 100:343-349, 2008). Initial studies were performed in fXI-deficient plasma supplemented with CTI, a trypsin inhibitor that selectively binds and inhibits fXII and fXIIa in plasma (Kambhu et al., J. Lab. Clin. Med. 105:625-628, 1985). Different sources of fXI-deficient plasma were tested, including plasma from a patient homozygous for a null mutation in the fXI gene. All plasmas tested gave similar results, and subsequent studies used a single source of plasma. fXI was added immediately before addition of calcium and an initiator of coagulation (TF, α-thrombin or fXa). When CTI was not included, thrombin generation was observed in some (but not all) reactions without an initiator, consistent with fXI activation by fXIIa. In addition, some fXI preparations promoted thrombin generation in the absence of an initiator even when CTI was present. This is consistent either with fXIa contamination of fXI, or incomplete inhibition of fXIIa by CTI. To remove fXIa activity from fXI, the proteins were treated with DFP, which irreversibly inhibits fXIa by reacting with the active site serine. When DFP-treated fXI was added to fXI-deficient plasma with CTI, thrombin generation was not observed after recalcification in the absence of an initiator over a 2-hour period. These results indicate that (1) CTI is required to prevent fXI activation by fXIIa in this system and (2) DFP treatment decreases fXIa contamination of fXI preparations sufficiently to prevent initiator-independent thrombin generation. Based on these results, CTI was included in all reactions, and all preparations of fXI were treated with DFP before use.

Assays measuring thrombin generation or clot resistance to fibrinolysis are insensitive to fXI when reactions are initiated by ≥5 pM TF (von dem Borne et al., Thromb. Haemost. 78:834-839, 1997; Cawthern et al., Blood 91:4581-4592, 1998; Keularts et al., Thromb. Haemost. 85:1060-1065, 2001; Ghosh et al., Blood Coagul. Fibrinolysis. 19:577-580, 2008). In the system described herein, the contribution of fXI to thrombin generation was not observed until TF was <1.6 pM (FIG. 1A). At 0.23 pM TF, the fXI-dependence of thrombin generation is easily observed (FIG. 1B), and this concentration was used in subsequent experiments. The results in FIG. 1C show that thrombin generation in plasma treated with 0.23 pM TF is significantly greater in the presence of fXI than in its absence (AUC 810±174 and 180±20 nM, respectively), while at 1.6 pM TF thrombin generation is similar in the presence and absence of fXI (AUC 1160±79 and 1131±78 nM, respectively). Consistent with this, thrombin generation occurred earlier and was greater in the presence of fXI, when reactions were initiated with 6 pM factor Xa (FIG. 1D), but was not fXI-dependent in reactions initiated by 30 pM factor Xa (FIG. 1D).

These findings support a model in which a protease generated after addition of TF to plasma activates fXI. That this protease may be thrombin, is supported by the observation that adding 5 nM α-thrombin to plasma promotes fXI-dependent thrombin generation (FIG. 1E). The α-thrombin initiator, at this concentration, does not cleave the fluorogenic substrate significantly, and the observed signal is due to activation of endogenous prothrombin. Interestingly, unlike the situation with TF and factor Xa, a fXI-dependent component of thrombin generation is still detectable even when larger amounts of α-thrombin are added.

Thrombin generation requires factor IX activation by factor XIa

The contribution of fXIa to hemostasis is thought to be largely, if not exclusively, due to its capacity to activate factor IX. To confirm the importance of factor IX activation by fXIa in the current model, fXI-deficient plasma was supplemented with recombinant fXI, followed by addition of TF. Previously, it was shown that wild type fXI (fXI$^{WT}$) and plasma fXI have similar activities in a variety of assays (Sun et al., J. Biol. Chem. 274:36373-36378, 1999; Sun & Gailani, J. Biol. Chem. 271:29023-29028, 1996). fXI$^{WT}$ consistently produced a higher peak thrombin generation than plasma fXI (compare FIGS. 2A and 1C), although the total thrombin generation (AUC) was only modestly greater (1267±20 vs. 810±174 nM thrombin, respectively). In the current studies, fXI$^{WT}$ was activated faster than plasma fXI in purified systems, perhaps due to differences in glycosylation, and possibly explaining the differences in the shapes of the thrombin generation curves. Two fXI variants that are poor activators of factor IX were compared to fXI$^{WT}$. fXI-Ala$^{195-197}$ is activated normally, but has a low affinity for factor IX due to alanine substitutions in a critical site on the A3 domain (Sun et al., J. Biol. Chem. 274:36373-36378, 1999). In fXI-Ala$^{557}$, the active site serine has been replaced with alanine (Aktimur et al., J. Biol. Chem. 278:7981-7987, 2003). fXIa-Ala$^{557}$, therefore, lacks enzymatic activity while still able to bind factor IX (Aktimur et al., J. Biol. Chem. 278:7981-7987, 2003). fXI- Ala$^{195-197}$ or fXI-Ala$^{557}$ demonstrated low specific activity (<5% of fXI$^{WT}$) in the zymogen (fXI) and activated (fXIa) forms in plasma clotting assays, and did not support thrombin generation in a CAT assay (AUC <100 nM for both proteins) (FIG. 2A).

While some data from purified (Oliver et al., *Arterioscler. Thromb. Vasc. Biol.* 19:170-177, 1999) and plasma (Wielders et al., *Arterioscler. Thromb. Vasc. Biol.* 24:1138-1142, 2004) systems indicates that platelets are required for fXII-independent fXI activation and activity, a recent study (Pedicord et al., *Proc. Natl. Acad. Sci. U.S.A.* 104:12855-12860, 2007) did not support this conclusion. Thus, thrombin generation in the presence of phospholipid and human platelets was compared (100,000/mm$^3$), and no appreciable difference between the two reactions (AUC 764 and 699 nM thrombin, respectively for fXI$^{WT}$) was found (FIGS. 2A and B). fXI has been shown to bind to platelet glycoprotein 1b (GP1b) (Baglia et al., *J. Biol. Chem.* 279:45470-45476, 2004). Inclusion of an antibody that blocks GP1b did not affect thrombin generation in the CAT assay, again consistent with the premise that platelets are not required for optimal fXI activation in this system.

Factor XI-Ala$^{83-84}$ in plasma clotting assays and thrombin generation assays To this point, the results support a model in which fXI is activated by a protease generated early in coagulation such as thrombin, with fXIa subsequently promoting thrombin generation by activating factor IX. However, other possibilities need to be considered. For example, the initiator may generate sufficient thrombin to activate factors V and VIII, allowing traces of fXIa to promote thrombin generation despite attempts to eliminate fXIa prior to the start of the assay. Thrombin generation was assessed in fXI-deficient plasma supplemented with fXI-Ala$^{83-84}$. Previous work demonstrated a binding site for α-thrombin on the fXI A1 domain (Baglia & Walsh, *J. Biol. Chem.* 271:3652-3658, 1996). A saturation mutagenesis approach subsequently determined that replacing Lys$^{83}$ and Gln$^{84}$ with alanine resulted in 100-fold lower affinity for α-thrombin compared with fXI$^{WT}$. In solution, fXI-Ala$^{83-84}$ was activated by fXIIa at about 65% of the rate of fXI$^{WT}$, but only at about 10% of the rate for fXI$^{WT}$ by α-thrombin (FIG. 3A). In a contact activation initiated clotting assay, fXI-Ala$^{83-84}$ had 100-150% of the specific activity of fXI$^{WT}$, indicating it is activated by fXIIa, and subsequently activates factor IX. Pre-activated XI-Ala$^{83-84}$ (fXI-Ala$^{83-84}$) had 70-100% of the clotting activity of fXIa$^{WT}$, confirming the ability of the protease to activate factor IX in plasma. In thrombin generation assays initiated with α-thrombin, fXI-Ala$^{83-84}$ supported thrombin generation poorly (AUC 111 nM) (FIG. 3B), consistent with the premise that fXI is activated by thrombin in this system.

Sensitivity of the CAT assay to fXIa

Figure 4A:
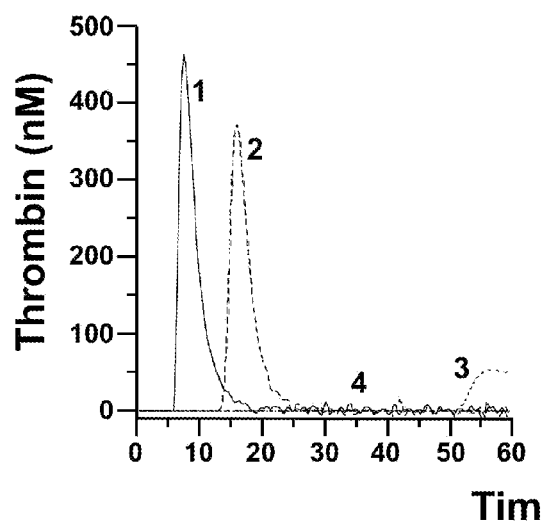
FIGS. 4A and 4B are graphs showing the effect of fXIa on thrombin generation in fXI-deficient plasma. Shown is thrombin generation in fXI-deficient plasma supplemented with (A) vehicle or (B) 30 nM fXI. Coagulation was initiated with (1) 300, (2) 30, (3) 3.0, or (4) 0.3 pM fXIa.
Figure 4B:
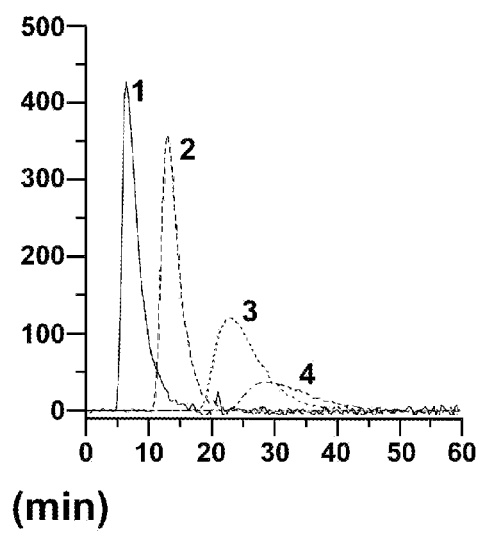

Robust thrombin generation was detected in fXI-deficient plasma supplemented with fXIa to a final concentration of 30 pM (0.1% of plasma fXI concentration) (FIG. 4A). At 3 pM fXIa, delayed thrombin generation was seen in some experiments, and was not observed with 0.3 pM fXIa. In contrast, in plasma containing DFP-treated fXI, 0.3 pM fXIa reproducibly initiated thrombin generation (FIG. 4B, AUC 441 nM thrombin) comparable to 5 nM α-thrombin (FIG. 1E, 549±178 nM thrombin). If it is postulated that the results in FIG. 4B are due to fXIa contamination of the fXI used to supplement the plasma, the contamination would apparently need to be sufficient to produce a final fXIa concentration in excess of 3 pM. That thrombin generation was observed after adding fXIa to a concentration well below this threshold (0.3 pM), but not in the absence of the fXIa, is compelling evidence that fXIa is generated in the plasma after addition of the initiator. Time to peak thrombin generation was longer with 0.3 pM fXIa than with TF or α-thrombin (compare FIGS. 4B, 1C and 1E), consistent with fXIa generating a small amount of thrombin through factor IX activation, which then converts fXI to fXIa, resulting in a subsequent larger burst of thrombin generation.

Thrombin generation in XII-Deficient plasma triggered by TF or thrombin

The results of the previous experiments were verified in a second system using fXII-deficient plasma, where endogenous fXI has not been exposed to fXIIa, effectively preventing contact activation-mediated generation of fXIa during preparation of plasma. Exogenous fXI is not required in this system, and an antibody against human fXI (O1A6) was used to generate the equivalent of a fXI-deficient state when required. O1A6 markedly prolongs the PTT clotting time of normal human plasma (Tucker et al., *Blood* 113(4):936-944, 2009; PCT Publication No. WO 2009/067660). Recombinant chimeras of fXI and the related protein PK (Sun & Gailani, *J. Biol. Chem.* 271:29023-29028, 1996) were used to localize the binding site for O1A6 to the fXI A3 domain (FIG. 5A). Subsequent studies with a panel of site-directed fXI mutants showed that O1A6 binds to, or blocks access to residues 183 through 197, which are required for factor IX binding (Sun et al., *J. Biol. Chem.* 274:36373-36378, 1999).

Figure 6A:
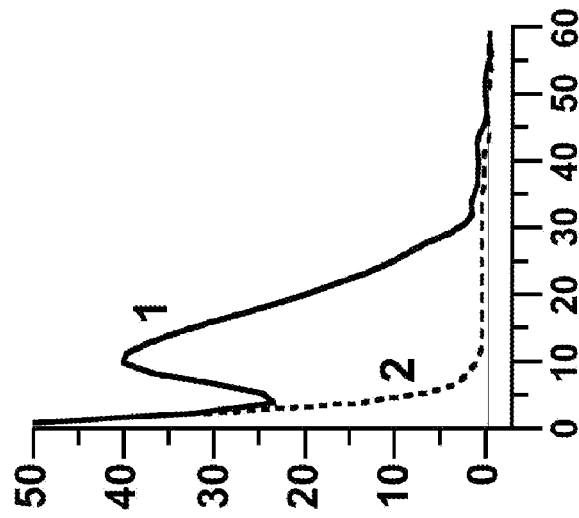
FIGS. 6A-6C are graphs showing the effect of anti-fXI IgG O1A6 on thrombin generation in fXII-deficient plasma. Shown is thrombin generation in fXII-deficient plasma in which coagulation was initiated by addition of $Ca^{2+}$ and (A) 0.23 pM TF, (B) 5 nM α-thrombin or (C) 10 nM α-thrombin in the absence (curves marked 1) or presence (curves marked 2) of 50 nM anti-human fXI IgG O1A6.
Figure 6B:
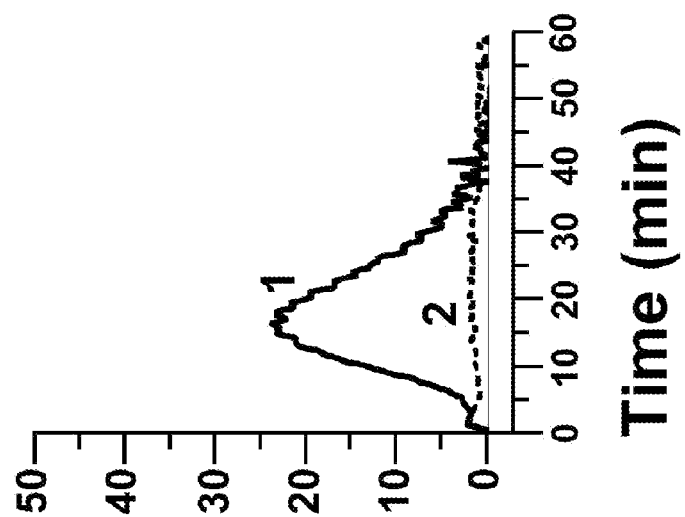
Figure 6C:
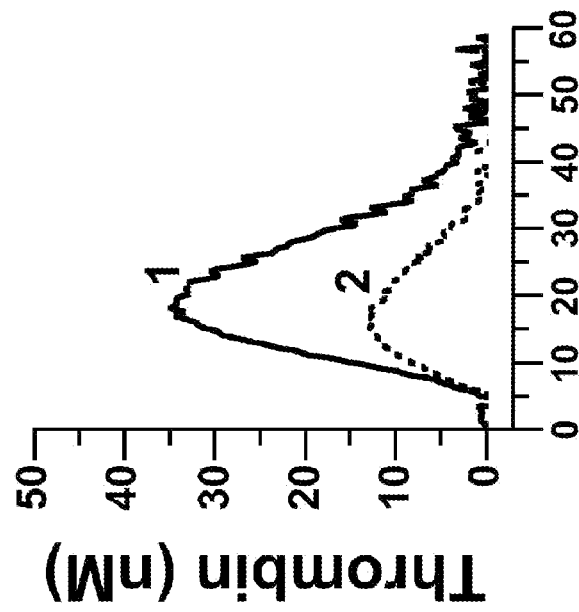

Thrombin generation was observed in fXII-deficient plasma to which 0.23 pM TF (FIG. 6A) or 5 nM α-thrombin (FIG. 6B) was added. Similar to results with fXI-deficient plasma, this process requires fXI/fXIa, as addition of O1A6 reduced thrombin generation (FIGS. 6A and 6B). A similar effect was achieved by depleting fXII-deficient plasma of fXI by antibody-affinity chromatography (Gailani & Broze, *Blood* 82:813-819, 1993), and adding back DFP-treated fXI restored thrombin generation. When a large amount of α-thrombin (50 nM) was added to the system, a fXI-dependent component of thrombin generation was still observed. In FIG. 6C, the initial signal (abutting the ordinate) is due to cleavage of substrate by the exogenous α-thrombin. Note the subsequent peak of thrombin generation, and its absence when O1A6 is included in the reaction. The findings support the premise that fXI is activated in the fXII-deficient plasma assays by thrombin and contributes to subsequent thrombin generation.

The sensitivity of the CAT assay in the fXII-deficient system was also compared to fXIIa. Interestingly, the system was considerably less sensitive to fXIIa than to fXIa. While subpicomolar concentrations of fXIa stimulated thrombin generation, concentrations of fXIIa in the 0.1 to 1 nM range were required to reproducibly produce similar effects (FIG. 7A). Addition of CTI completely blocked thrombin generation initiated by fXIIa. Antibody 14E11, which binds to the fXI A2 domain (FIG. 5B) prolongs the PTT clotting time of murine and human plasma, but does not affect clotting induced by fXIa, indicating it interferes with fXI activation but not fXIa activity. In solution, 14E11 partially inhibits fXIIa activation of fXI in solution (FIG. 5C), and significantly reduced fXIIa-initiated thrombin generation (FIG. 7A), but did not affect thrombin generation triggered by TF or α-thrombin (FIG. 7B). This, again, supports the notion that fXI activation in this system does not involve fXIIa.

Example 5

Treatment of a Subject with Thrombosis by Administration of fXI-Specific Antibody 14E11

This example describes a representative method for the treatment of a subject with thrombosis by administration of a therapeutically effective amount of monoclonal antibody 14E11.

A patient diagnosed with thrombosis is administered approximately 1 mg/kg 14E11 in a pharmaceutically acceptable carrier. The antibody is administered intravenously by bolus injection. The patient can receive either a single dose, or additional doses can be administered as needed. The dose of 14E11 can also be altered as needed depending on the severity of the disease, as well as the age, weight and general health of the subject. An appropriate dose and administration schedule can be determined by a skilled practitioner.

Example 6

Treatment of Metastatic Cancer with Monoclonal Antibody 14E11

This example describes a representative method for the treatment of a subject with metastatic cancer.

A patient diagnosed with metastatic cancer (such as, but not limited to, breast cancer, liver cancer, lung cancer, pancreatic cancer or melanoma) is administered a primary treatment, such as radiation treatment or chemotherapy. The patient is further administered fXI-specific monoclonal antibodyl-4E11 as an adjunctive therapy. 14E11 can be administered prior to, concurrently with, or following the primary treatment. Furthermore, 14E11 can be administered in a single dose or repeated as necessary to treat the metastatic cancer (for example, reduce tumor size, slow tumor growth or inhibit further metastasis). Typically, 14E11 is administered intravenously by bolus injection, but can be administered using any other appropriate route of administration depending in part on the cancer to be treated. An appropriate dose of 14E11 can be determined by a skilled practitioner, but is generally about 0.1 to about 10 mg/kg.

Example 7

Treatment of Decompression Disease by Administration of 14E11

This example describes a representative method for the treatment of a subject decompression disease.

A patient suffering from decompression disease is treating using a standard primary treatment, such as exposure to 100% oxygen or hyperbaric oxygen therapy. The patient is further administered fXI-specific monoclonal antibody 14E11 as an adjunctive therapy. 14E11 can be administered prior to, concurrently with, or following the primary treatment. Furthermore, 14E11 can be administered in a single dose or repeated as necessary to treat or ameliorate one or more symptoms of decompression disease. Typically, 14E11 is administered intravenously by bolus injection, but can be administered using any other appropriate route of administration. An appropriate dose of 14E11 can be determined by a skilled practitioner, but is generally about 0.1 to about 10 mg/kg. In some cases, if the patient is suffering from a mild form of decompression disease, the patient can forego 100% oxygen treatment and/or hyperbaric oxygen therapy and receive 14E11 as the primary treatment.

In view of the many possible embodiments to which the principles of the disclosed subject matter may be applied, it should be recognized that the illustrated embodiments are only preferred examples of the disclosure and should not be taken as limiting the scope of the disclosure. Rather, the scope of the disclosure is defined by the following claims.

The invention claimed is:

1. An isolated nucleic acid molecule encoding a monoclonal antibody, or an antigen-binding fragment thereof, specific for coagulation factor XI (fXI), wherein:
   the variable light chain ($V_L$) of the antibody comprises amino acids 24-34, 50-63 and 91-98 of SEQ ID NO: 1; and
   the variable heavy chain ($V_H$) of the antibody comprises amino acids 31-35, 50-68 and 98-105 of SEQ ID NO: 3.

2. The isolated nucleic acid molecule of claim 1, wherein the nucleotide sequence encoding the $V_L$ of the monoclonal antibody comprises SEQ ID NO: 2.

3. The isolated nucleic acid molecule of claim 1, wherein the nucleotide sequence encoding the $V_H$ of the monoclonal antibody comprises SEQ ID NO: 4.

4. An expression vector comprising the isolated nucleic acid molecule of claim 1.

5. An isolated host cell transformed with the nucleic acid molecule of claim 1.

6. The isolated nucleic acid molecule of claim 1, wherein the nucleotide sequence encoding the $V_L$ is at least 95% identical to SEQ ID NO: 2.

7. The isolated nucleic acid molecule of claim 1, wherein the nucleotide sequence encoding the $V_H$ is at least 95% identical to SEQ ID NO: 4.

8. The isolated nucleic acid molecule of claim 1, wherein the nucleotide sequence encoding the $V_L$ of the monoclonal antibody comprises SEQ ID NO: 2 and the nucleotide sequence encoding the $V_H$ of the monoclonal antibody comprises SEQ ID NO: 4.

9. The isolated nucleic acid molecule of claim 1, wherein the antibody is a Fab fragment, a Fab' fragment, a F(ab)'$_2$ fragment, a single chain Fv protein (scFv), or a disulfide stabilized Fv protein (dsFv).

10. The isolated nucleic acid molecule of claim 1, wherein the antibody is an IgG.

11. A composition comprising the nucleic acid molecule of claim 1 and a pharmaceutically acceptable carrier.

12. An isolated nucleic acid molecule encoding an immunoconjugate comprising a monoclonal antibody, or an antigen-binding fragment thereof, specific for fXI and a fusion partner, wherein:
   the variable light chain ($V_L$) of the antibody comprises amino acids 24-34, 50-63 and 91-98 of SEQ ID NO: 1; and
   the variable heavy chain ($V_H$) of the antibody comprises amino acids 31-35, 50-68 and 98-105 of SEQ ID NO: 3.

* * * * *